United States Patent
Tam et al.

(10) Patent No.: US 6,768,028 B2
(45) Date of Patent: Jul. 27, 2004

(54) HYDROFORMYLATION OF UNSATURATED COMPOUNDS USING POLYMERIC PHOSPHITE LIGANDS

(76) Inventors: Wilson Tam, 3781 Brookcroft La., Boothwyn, PA (US) 19061; Kathryn Eileen Schwiebert, 4801 Pennington Ct., Wilmington, DE (US) 19808; Joe Douglas Druliner, 33 Bridleshire Rd., Newark, DE (US) 19771

(*) Notice: Subject to any disclaimer, the term of this patent is extended or adjusted under 35 U.S.C. 154(b) by 290 days.

(21) Appl. No.: 10/150,214

(22) Filed: May 17, 2002

(65) Prior Publication Data

US 2002/0177737 A1 Nov. 28, 2002

Related U.S. Application Data

(62) Division of application No. 09/399,634, filed on Sep. 20, 1999, now Pat. No. 6,420,611.

(51) Int. Cl.$^7$ .............................................. C07C 45/50
(52) U.S. Cl. ..................... 568/454; 568/451
(58) Field of Search .................................. 568/451, 454

(56) References Cited

U.S. PATENT DOCUMENTS

| | | | |
|---|---|---|---|
| 3,496,215 A | 2/1970 | Drinkard et al. | 260/465.8 |
| 3,631,191 A | 12/1971 | Kane et al. | 260/439 |
| 3,655,723 A | 4/1972 | Drinkard et al. | 260/465.3 |
| 3,766,237 A | 10/1973 | Chia et al. | 260/465.3 |
| 4,434,302 A | 2/1984 | De Munck et al. | 508/454 |
| 5,432,289 A | 7/1995 | Pugin et al. | 549/221 |
| 5,512,696 A | 4/1996 | Kreutzer et al. | 558/338 |
| 5,543,536 A | 8/1996 | Tam | 556/13 |
| 5,573,641 A | 11/1996 | Meade et al. | 162/158 |
| 5,663,369 A * | 9/1997 | Kreutzer et al. | 549/212 |
| 5,688,986 A | 11/1997 | Tam et al. | 558/338 |
| 5,723,641 A | 3/1998 | Tam et al. | 556/13 |
| 5,874,641 A * | 2/1999 | Burke et al. | 568/454 |
| 6,284,865 B1 * | 9/2001 | Tam et al. | 528/287 |

FOREIGN PATENT DOCUMENTS

| | | |
|---|---|---|
| EP | 0 877 029 | 11/1998 |
| WO | 93/03839 | 3/1993 |
| WO | 99/06146 | 2/1999 |
| WO | 99/62855 | 9/1999 |
| WO | 00/21663 | 4/2000 |

OTHER PUBLICATIONS

T. Jongsma, P. Kimkes and G. Challa, A new type of highly active polymer–bound rhodium hydroformylation catalyst, *Polymer*, 33, No. 1, 161–165, 1992.

Achim Kless, Claudia Lefeber, Anke Spannenberg, Rhett Kempe, Wolfgang Baumann, Jens Holz and Armin BÖrner, The Chiral Early–Late Hetrobimetallic Complex –A Titanium(IV)–Palladium(II) Complex Based on Salenophos, *Tetrahedron*, 52, No. 46, 14599–14606, 1996.

Gregory D. Cuny and Stephen L. Buchwald, Practical, High–Yield, Regioselective, Rhodium–Catalyzed Hydroformylation of Functionalized α–Olefins, *J.Am. Chem. Soc.*, 115, 2068–2070, 1993.

Richard A. Bartsch, Yung Liu, Sang Ihn Kang, Byungki Son, Gwi Suk Heo, Paul G. Hipes and Lyndra J. Bills, Synthesis of Highly Lipophilic Crown Ether Carboxylic Acids, *J. Org, Chem.*, 48, 4864–4869, 1983.

Leonard E. Miller, W. W. Hanneman, W.L. Sr. John and R.R. Smeby, The Reactivity of the Methyl Group in 2–Methyl–3–nitronaphthalene, *JACS*, 76,296–297, 1954.

Warren W. Kaeding, Oxidation of Phenols with Cupric Salts, *JOC*, 28, 1063–1067, Apr. 1963.

Fukiko Yamada, Tomihiro Nishiyama, Masahiro Yamamoto and Kazunori Tanaka, Substituted Bisphenols as Antioxidants for Autoxidation of Tetralin, *Bull, Chem. Soc. Jpn.*,62, 3603–3608, Nov. 1989.

Wei–Bo Wang, Li–Lan Shi and Yao–Zeng Huang, An Efficient SbC13–Metal System For Allylation, Reduction and Acetalization of Aldehydes, *Tetrahedron*, 46, No. 9, 3315–3320, 1990.

Martin Hovorka, Jana Günterova and Jiri Zavada, Highly Selective Oxidative Cross–Coupling of Substituted 2–naphthols: A Concenient Approach to Unsymmetrical 1, 1'–binaphthalene–2,2'–diols, *Tetrahedron*, 31, No. 3, 413–416, 1990.

Harold R. W. Ansink, Erwin Zelvelder and Hans Cerfontain, Sulfonation of a series of naphthalenes containing two differens oxy substitutuents, *Recl. Trav. Chim. Pays–Bas*, 112, 216–225, 1993.

Donald L. Jameson SHaron E. Hilgen, Conrad E. Hummel and Susan L. Pichla, Design and Sythesis of a Series of Facially Coordinating Tridentate Ligands Containing an H20 Donor Atom Set, *Tetrahedron*, 30, No. 13, 1609–1612, 1989.

Anderson de Farias Dias, An Improved High Yield Synthesis of Dehydrodieugenol, *Phytochemistry*, 27, No. 9, 3008–3009, 1988.

(List continued on next page.)

Primary Examiner—Sreeni Padmanabhan
Assistant Examiner—Sikarl A. Witherspoon

(57) ABSTRACT

A composition and a process for using the composition in hydroformylation of unsaturated organic compounds are disclosed. The composition comprises a Group VIII metal and a phosphite-containing polymer having repeat units derived from (1) a carbonyl compound, a monomer, and phosphochloridite; (2) phosphorus trichloride, a polyhydric alcohol, and an aromatic diol; or (3) combinations of (1) and (2). The process comprises contacting an unsaturated compound, in the presence of the composition disclosed herein, with a fluid comprising hydrogen.

21 Claims, No Drawings

OTHER PUBLICATIONS

J. Gloede, B. Costisella and H. Gross, Zur Halogenierung der o–Methoxyphenylester von P'''–Säuren, *Z. anotg. allg. Chem.*, 535, 221–228, 1986.

W. Hewertson, B. C. Smith and R. A. Shaw, Diphenyl Phosphorochloridite (Diphenyl Monochlorophosphite), Inorganic Syntheses, Chapter 17, 68–71.

Giovanni Casiraghi, Guiseppe Casnati, Andrea Pochini, Guiseppe Puglia, Rocco Ungaro adn Giovanni Sartori, Uncatalyzed Phenol–formaldehyde Reactions. A Convenient Synthesis of Substituted 2,2'–Dihydroxy–diphenyl-methanes, *Communications*, 143–145, Feb. 1981.

MIchael J. Baker, Karl N. Harrison, A. Guy Orpen, Paul G. Pringle and Gordon Shaw, Chelating Diphosphite Complexes of Nickel(0) and Plainum(0): Their Remarkable Stability and Hydrocyanation Activity, *J. Chem. Soc. CHEM. COMMUN.*, 803–804, 1991.

Michael J. Baker and Paul G. Pringle, Chiral Aryl Diphosphites: a New Class of Ligands for Hydrocyanation Catalysis, *J. Chem. Soc., CHEM. COMMUN.*, 1292–1293, 1991.

* cited by examiner

US 6,768,028 B2

HYDROFORMYLATION OF UNSATURATED COMPOUNDS USING POLYMERIC PHOSPHITE LIGANDS

This application is a division of application Ser. No. 09/399,634, filed Sep. 20, 1999 now U.S. Pat. No. 6,420,611.

FIELD OF THE INVENTION

This invention relates to a process for the preparation of aldehydes by hydroformylation of unsaturated organic compounds in the presence of a Group VIII metal and selected polymeric phosphite ligands. The invention also relates to composition of selected hydroformylation catalysts derived from polymeric phosphite ligands and Group VIII metal.

BACKGROUND OF THE INVENTION

Phosphorus-based ligands are ubiquitous in catalysis and are used for a number of commerically important chemical transformations. Phosphorus-based ligands commonly encountered in catalysis include phosphines and phosphites. These ligands include monophosphine and monophosphite ligands, which are compounds that contain a single phosphorus atom that serves as a donor to a transition metal, and bisphosphine, bisphosphite, and bis(phosphorus) ligands, which contain two phosphorus donor atoms and normally form cyclic chelate structures with transition metals.

An industrially important catalytic reaction using phosphorus-based ligands of particular importance is olefin hydroformylation. Phosphite ligands are particularly good ligands for these reactions. For example, U.S. Pat. No. 5,235,113 describes a hydroformylation process in which an organic bidentate ligand containing two phosphorus atoms linked with an organic dihydroxyl bridging group is used in a homogeneous hydroformylation catalyst system also comprising rhodium. See also Cuny et al., *J. Am. Chem. Soc.,* 1993, 115, 2066; U.S. Pat. Nos. 4,769,498; 4,668,651; 4,885,401; 5,113,022; 5,059,710; 5,235,113; 5,264,616; 4,885,401; and published international applications WO-A-9303839 and WO-A-9518089.

Hydroformylation processes involving organic bidentate ligands containing two trivalent phosphorus atoms, in which the two phosphorous atoms are linked with a 2,2'-dihydroxyl-1,2'-binaphthalene bridging group, are described in U.S. Pat. No. 5,874,641 and the prior art referenced therein. U.S. Pat. No. 5,874,641 describes ligands containing substituents such as esters or ketones on the 3,3'-positions of the 2,2'-dihydroxyl-1,1'-binaphthalene bridging group. Such ligands provide reasonably good selectivity in the hydroformylation of internal olefins to terminal aldehydes.

Recovery of the ligand and catalyst is important for a successful process. Typical separation procedures to remove the product(s) from the catalyst and ligand involve extraction with an immiscible solvent or distillation. It is usually difficult to recover the catalyst and ligand quantitatively. For instance, distillation of a volatile product from a non-volatile catalyst results in thermal degradation of the catalyst. Similarly, extraction results in some loss of catalyst into the product phase. For extraction, one would like to be able to tune the solubility of the ligand and catalyst to disfavor solubility in the product phase. These ligands and metals are often very expensive and thus it is important to keep such losses to a minimum for a commercially viable process.

One method to solve the problem of catalyst and product separation is to attach the catalyst to an insoluble support. Examples of this approach have been previously described, and general references on this subject can be found in "Supported Metal Complexes", D. Reidel Publishing, 1985, Acta Polymer., 1996, 47, 1; Comprehensive Organometallic Chemistry, Pergamon Press, 1982,553; *J. of Mol. Catal. A,* 104, 1995, 17–85 and *Macromol. Symp.* 80, 1994, 241. Specifically, monophosphine and monophosphite ligands attached to solid supports are described in these references. Bisphosphine ligands have also been attached to solid supports and used for catalysis, as described in for example U.S. Pat. No. 5,432,289; *J. Mol. Catal. A,* 112, 1996, 217; and *J. Chem. Soc., Chem. Commun.,* 1996, 653. The solid support in these prior art examples can be organic, e.g., a polymer resin, or inorganic in nature.

Polymer-supported multidentate phosphorus ligands may be prepared by a variety of methods known in the art. See U.S. Pat. Nos. 4,769,498 and 4,668,651 and published international applications WO9303839 and WO9906146 and EP 0864577 A2 and EP0877029 A2. These prior art disclose side-chain polymers containing multidentate phosphorus ligands as pendant groups.

The present invention involves another approach to improving recovery of the catalyst by providing polymeric forms of the bidentate ligands themselves.

There is an increasing need to develop a catalytic process in which the loss of catalyst composition can be substantially reduced during separation of product from the catalyst. An object of the invention is to provide a hydroformylation process. An advantage of the invention is that varying the molecular weight and degree of branching can control the solubility of the catalyst composition. Another advantage of the invention is that the catalyst composition can be substantially recovered by, for example, filtration. Other objects and advantages of the present invention will become apparent as the invention is more fully disclosed below.

SUMMARY OF THE INVENTION

According to a first embodiment of the invention, a process is provided. The process comprises contacting, in the presence of a catalyst, an unsaturated organic compound with a fluid containing hydrogen and carbon monoxide under a condition sufficient to produce an aldehyde wherein said catalyst is selected from the group consisting of catalyst A, catalyst B, and combinations thereof. Catalyst A comprises a Group VIII metal and polymer A that comprises repeat units derived from (1) a carbonyl compound, (2) a monomer, and (3) phosphochloridite. Catalyst B comprises a Group VIII metal and polymer B which comprises repeat units derived from (1) phosphorus trichloride, (2) a polyhydric alcohol, and (3) an aromatic diol.

According to a second embodiment of the invention, a composition is provided that comprises a Group VIII metal and a phosphite polymeric composition selected from the group consisting of polymer A, polymer B, and combinations thereof; the polymer A comprises repeat units derived from (1) a carbonyl compound, (2) a monomer, and (3) phosphochloridite; and the polymer B comprises repeat units derived from (1) phosphorus trichloride, (2) a polyhydric alcohol, and (3) an aromatic diol.

DETAILED DESCRIPTION OF THE INVENTION

The polymeric phosphite composition is also referred to herein as ligand. The ligands suitable for use in the process of the invention are polymer A and polymer B. Polymer A comprises repeat units derived from (1) a carbonyl compound, (2) a monomer, and (3) phosphorochloridite. The monomer is selected from the group consisting of a first polyhydric alcohol, an amine, and combinations thereof. Polymer B comprises repeat units derived from (1) phosphorus trichloride, (2) a second polyhydric alcohol, and (3) an aromatic diol.

The carbonyl compound has the formula of $(R^1O_2C)_m(OH)—Ar^1—(OH)(CO_2R^1)_m$, $(R^1O_2C)_m(OH)—Ar^2—A^2—Ar^2—(OH)(CO_2R^1)_m$, $(R^1O_2C)_m(OH)—Ar^2—Ar^2—(OH)(CO_2R^1)_m$, and combinations of two or more thereof.

The term "polyhydric alcohol" used herein refers to, unless otherwise indicated, a molecule having two or more hydroxyl groups. Generally a polyhydric alcohol can be selected from the group consisting of dialcohols, trialcohols, tetraalcohols, and combinations of two or more thereof.

The first polyhydric alcohol has the formula selected from the group consisting of $(HO)_m—A^1—(OH)_m$, $(HO)_m—Ar^2—A^1—Ar^2—(OH)_m$, $(HO)_m—Ar^2—(O)—A^1—(O)—Ar^2—(OH)_m$, $(HO)_m—(A^1—O)_p—A^1—(OH)_m$, $(HO—A^1)_m(OH)—Ar^1—(OH)(A^1—OH)_m$, $(HO—A^1)_m(OH)—Ar^2—A^2—Ar^2—(OH)(A^1—OH)_m$, $(HO—A^1)_m(OH)—Ar^2—Ar^2—(OH)(A^1—OH)_m$, $(HO)_m—Ar^2—(O—A^1)_p—O—Ar^2—(OH)_m$, $(OH)_m{}_{—Ar}{}^2—Ar^2—(OH)_m—Ar^2—A^2—(OH)_m$, $Ar^2—(OH)_m$, $(HO)_m—Ar^2—A^1—C(O)—O—A^1—O—C(O)—A^1—Ar^2—(OH)_m$, $(OH)—Ar^1—(OH)$, and combinations of two or more thereof.

Each $Ar^1$ is selected from the group consisting of $C_6$ to $C_{40}$ phenylene group, $C_{12}$ to $C_{40}$ biphenylene group, $C_{10}$ to $C_{40}$ naphthylene group, $C_{20}$ to $C_{40}$ binaphthylene group, and combinations of two or more thereof.

Each $Ar^2$ is independently selected from the group consisting of $C_6$ to $C_{40}$ phenylene group, $C_{10}$ to $C_{40}$ naphthylene group, and combinations thereof.

Each $A^1$ is independently selected from the group consisting of $C_1$ to $C_{12}$ alkylene groups.

Each $A^2$ is independently selected from the group consisting of $—C(R^1)(R^1)$, $—O—$, $—N(R^1)—$, $—S—$, $—S(O)—$, $—S(O)—$, and combinations of two or more thereof.

Each $R^1$ is independently selected from the group consisting of hydrogen, $C_1$ to $C_{12}$ alkyl or cycloalkyl group, $C_6$ to $C_{20}$ aryl group, and combinations of two or more thereof.

Each $R^2$ is independently selected from the group consisting of hydrogen, $C_1$ to $C_{12}$ alkyl or cycloalkyl group, acetal having 2 to about 20 carbon atoms, ketal having 2 to about 20 carbon atoms, $—OR^3$, $—CO_2R^3$, $C_6$ to $C_{20}$ aryl group, F, Cl, $—NO_2$, $—SO_3R^3$, $—CN$, perhaloalkyl having 1 to about 12 carbon atoms, $—S(O)R^3$, $—S(O)_2R^3$, $—CHO$, $—C(O)R^3$, cyclic ether having 2 to about 10 carbon atoms, $—A^1Z$, and combinations of two or more thereof;

each Z is selected from the group consisting of $—CO_2R^3$, $—CHO$, $—C(O)R^3$, $—C(O)SR^3$, $—SR^3$, $—C(O)NR^1R^1$, $—OC(O)R^3$, $—OC(O)OR^3$, $—N=CR^1R^1$, $—C(R^1)=NR^1$, $—C(R^1)=N—O—R^1$, $—P(O)(OR^3)(OR^3)$, $—S(O)_2R^3$, $—S(O)R^3$, $—C(O)OC(O)R^3$, $—NR^3CO_2R^3$, $—NR^3C(O)NR^1R^1$, F, Cl, $—NO_2$, $—SO_3R^3$, perhaloalkyl, $—CN$, and combinations of two or more thereof.

Each $R^3$ is independently selected from the group consisting of $C_1$ to $C_{12}$ alkyl or cycloalkyl group, $C_6$ to $C_{20}$ aryl group, and combinations thereof.

Each m is independently a number in the range of from 1 to 2.

Each p is independently a number in the range of from 1 to 10.

The presently preferred carbonyl compounds are diesters, diacids, or combinations thereof.

Examples of suitable diesters or diacids include, but are not limited to those shown below:

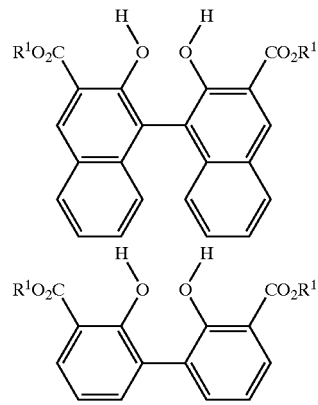

in which each $R^1$ is independently selected from the group consisting of hydrogen, $C_1$ to $C_{12}$ alkyl or cycloalkyl group, $C_6$ to $C_{20}$ aryl group, and combinations of two or more thereof. The other positions on the aromatic rings can also be substituted with an alkyl group, ether group, ester group, or combinations thereof.

Specific examples of suitable diesters or diacids include, but are not limited to, dialkyl 2,2'-dihydroxyl-1,1'-binaphthalene-3,3'-dicarboxylate, dialkyl 2,2'-dihydroxyl-1,1'-biphenyl-3,3'-dicarboxylate, 2,2'-dihydroxy-biphenyl-3,3'-dicarboxylic acid, 2,2'-dihydroxy-1,1'-binaphthyl-3,3'-dicarboxylic acid and combinations of two or more thereof.

The carbonyl compounds illustrated above can also be blended with one or more second carbonyl compounds such as, for examples, $(R^1O_2C)_m—Ar^1—(CO_2R^1)_m$, $(R^1O_2C)_m—A^1—(CO_2R^1)_m$, $(R^1O_2C)_m—Ar^2—A^1—Ar^2—(CO_2R^1)_m$, $(R^1O_2C)_m—Ar—(O)—A^2—(O)—Ar^2—(CO_2R^1)_m$, $(R^1O_2C)_m—(A^1—O)_p—A^1—(CO_2R^1)_m$, and combinations of two or more thereof.

Examples of the second carbonyl compounds that can be blended are terephthalic acid, isophthalic acid, phthalic acid, dimethyl isophthalate, dimethyl phthalate, dimethyl terephthalate.

The first polyhydric alcohol can be aromatic as in a phenol or aliphatic as in an alkyl alcohol and can contain two aromatic alcohols, two aliphatic alcohols, or one of each. The alcohol has the formula disclosed in the above.

Examples of the first polyhydric alcohols include, but are not limited to, those illustrated as follows.

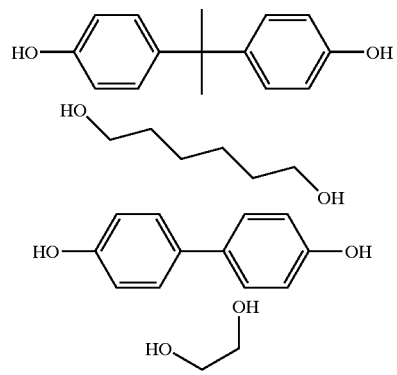

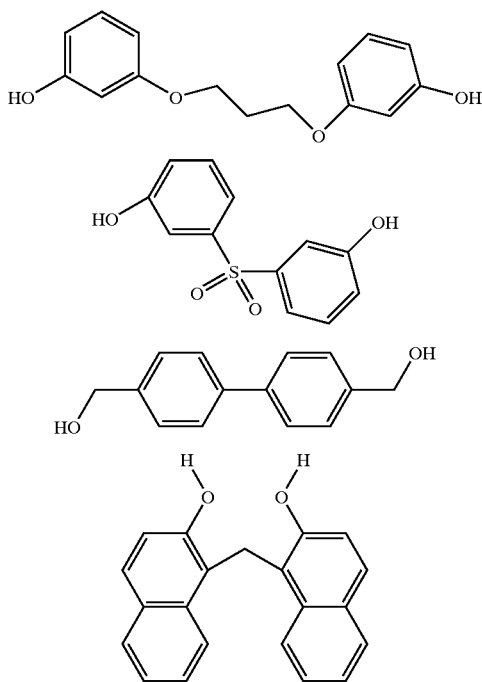

Other examples of the first polyhydric alcohols are hexa(ethylene glycol), 1,3-propananediol, tetra(ethylene glycol), 1,4-cyclohexanediol, 2,6-dihydroxynaphthalene, or combinations of two or more thereof.

In addition to the polyhydric alcohols shown above, compounds containing three or more hydroxy groups can be used. An example of such compound is 1,3,5-benzene tricarboxylic acid.

The monomer can also be an amine selected from the group consisting of diamines, triamines, tetraamines, and combinations of two or more thereof. The amine can be primary or secondary aliphatic amine. Some examples are 1,6-hexanediamine, N,N'-dimethylhexanediamine, 1,4-butanediamine, and combinations of two or more thereof.

The phosphochloridite has the formula of $ClP(O-Ar^2R^2)_2$, where the $Ar^2$ groups can be unlinked or linked directly to each other or with a group $A^2$ and the $R^2$ group is preferably ortho to the oxygen.

Examples of phosphorochloridite include, but are not limited to, those shown below.

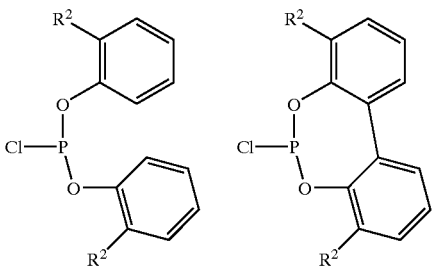

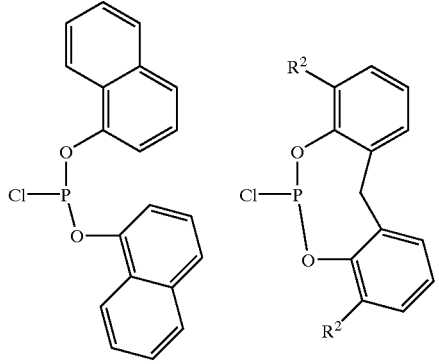

in which the other positions on the aromatic ring, i.e., para or meta to the oxygen atom, can also be substituted with alkyl, ether or ester groups, or combinations of two or more thereof.

Polymer A can be produced by any means known to one skilled in the art. A process that can be used for producing polymer A disclosed above comprises (1) contacting a carbonyl compound and a monomer under a condition sufficient to produce an intermediate and (2) contacting the intermediate with phosphorochloridite under a condition effective to produce the composition disclosed in the first embodiment of the invention.

The definition and scope of the carbonyl compound, monomer, and phosphochloridite are the same as those disclosed above and, for the interest of brevity, the description of which is omitted herein.

In the first step of the process, a carbonyl compound disclosed above is contacted with a monomer disclosed above to produce an intermediate that can be a polyester or a polyamide. The contacting can be carried out with any molar ratio of the monomer to carbonyl compound so long as the ratio is sufficient to produce the intermediate. The ratio generally can be in the range of from about 0.1:1 to about 10:1, preferably about 0.5:1 to about 5:1, and most preferably about 1:1 to about 2:1. Generally the process can be carried out with either an excess of monomer or equimolar amount of monomer to carbonyl compound. The ratio of reactive ester or acid to reactive alcohol or amine of one is most preferred.

Alternatively, the carbonyl compound can be combined with a second or other carbonyl compounds disclosed above. Additional examples of the second carbonyl compounds include, but are not limited to $(R^1O_2C)_m-Ar^1-(CO_2R^1)_m$, $(R^1O_2C)_m-A^1-(CO_2R^1)_m$, $(R^1O_2C)_m-Ar^2-A^1-Ar^2-(CO_2R^1)_m$, $(R^1O_2C)_m-Ar^2-(O)-A^1-(O)-Ar^2-(CO_2R^1)_m$, $(R^1O_2C)_m-(A^1-O)_p-A^1-(CO_2R^1)_m$, and combinations of two or more thereof.

The contacting can be carried out under any condition as long as the condition is sufficient to effect the production of the intermediate. Generally it includes a temperature in the range of from about 100° C. to about 450° C., preferably about 150° C. to about 350° C., and most preferably 180° C. to 270° C., under any pressure that can accommodate the temperature range, and for a sufficient time of about 1 minute to about 24 hours. The contacting can also be carried out neat or with an inert solvent such as tetraglyme.

The resulting intermediate can be then contacted with a phosphochloridite disclosed above to form the polymeric phosphite ligand. The contacting can be carried out, if desired, in a solvent such as toluene or tetrhydrofuran under a condition sufficient to effect the production of the composition. The contacting can be carried out in the presence of a base such as an organic base. The addition of base results in the formation of a salt formed by neutralizing HCl. Suitable bases can be organic amines. Especially preferred are trialkylamines. The most preferred bases are selected from the group consisting of tributylamine,- benzyldimethylamine, triethylamine, and diisopropylmethylamine. The contacting condition can include a temperature in the range of from about −50° C. to about 150° C., preferably about −40° C. to about 100° C., and most preferably, −30° C. to 80° C., under any pressure that can accommodate the temperature range, and for a sufficient time of about 1 minute to about 24 hours.

The molar ratio of the phosphochloridite to the alcohol group of the intermediate, can range from about 10:1 to about 0.5:1, preferably about 1:1.

The phosphorochloridite can be prepared by contacting at a temperature between about −40° C. and 10° C. about one molar equivalent of $PCl_3$ with about two molar equivalents of substituted phenol in the absence of a base such as an organic base. The resulting solution can be then contacted with at least two equivalents of a base such as an organic base to produce a phosphorochloridite. When the substituted phenols are replaced with substituted biphenol or substituted alkylidenebisphenol, the phosphorochloridite can be similarly prepared from initially contacting about one molar equivalent of $PCl_3$ with about one molar equivalent of substituted biphenol or substituted alkylidenebisphenol between about −40° C. and 10° C. in the absence of an organic base. The resulting solution is then contacted with at least two equivalents of a base such as organic base to produce a phosphorochloridite.

When preparing the phosphorochloridite in the above manner, it is desirable to maintain temperature in the −40° C. and 10° C. range during the base addition. The addition of base results in the formation of an insoluble salt formed by neutralizing HCl, the reaction mixture can become a thick slurry. Such a slurry can create problems in achieving good mixing of base, which can be important in avoiding temperature gradients in the reaction mixture that can decrease yield of the desired product. It is desirable, therefore, that the reaction be conducted with vigorous stirring or other agitation to allow effective removal of heat from the reaction mixture. Cooling to the disclosed temperature range can be accomplished by well-known techniques in the art.

The phosphochloridite can be prepared by a variety of other methods known to in the art, for example. One method involves treating phenols with $PCl_3$, such as described in *Polymer*, 1992, 33, 161; *Inorg. Syn.* 1996, 8, 68; U.S. Pat. No. 5,210,260; WO9622968 and *Z. Anorg. Allg. Chem.* 1986, 535, 221.

When the phosphorochloridite cannot be prepared in good yield from $PCl_3$, the preferred method involves the treatment of N,N-dialkyl diarylphosphoramidite derivatives with HCl. When the phosphorochloridite cannot be prepared in good yield from $PCl_3$, the preferred method involves the treatment of N,N-dialkyl diarylphosphoramidite derivatives with HCl. The N,N-dialkyl diarylphosphoramidite is of the form $(R^9)_2NP(aryloxy)_2$ where $R^9$ is a $C_1$ to $C_4$ alkyl group, and can be obtained by reacting phenol or substituted phenol with $(R^9)_2NPCl_2$ by methods known in the art, such as described in WO9622968, U.S. Pat. Nos. 5,710,306, and 5,821,378. The N,N-dialkyl diarylphosphoramidites may be prepared, for example, as described in *Tet. Lett.*, 1993, 34,6451; *Synthesis*, 1988, 2, 142–144, and *Aust. J. Chem.*, 1991, 44, 233.

Non limiting examples of the production of the intermediate, i.e., polyester or polyamide, are shown below.

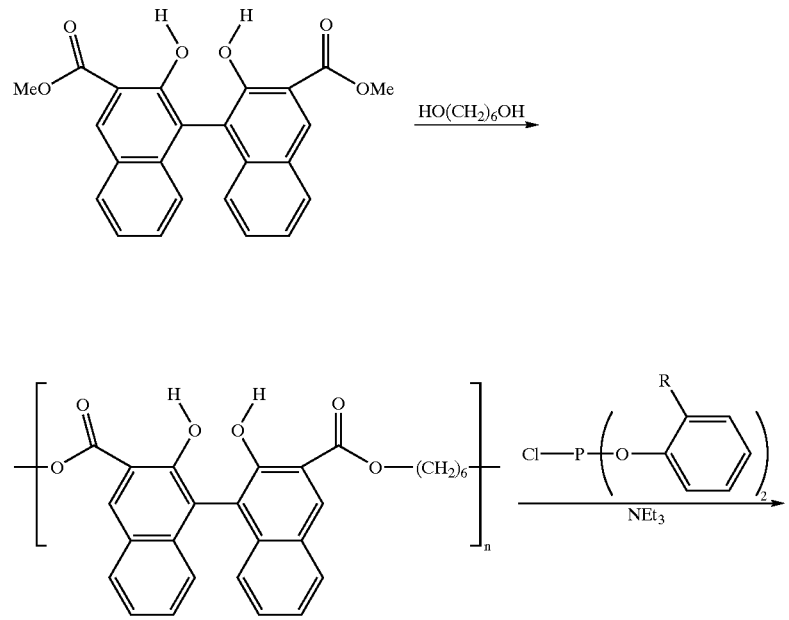

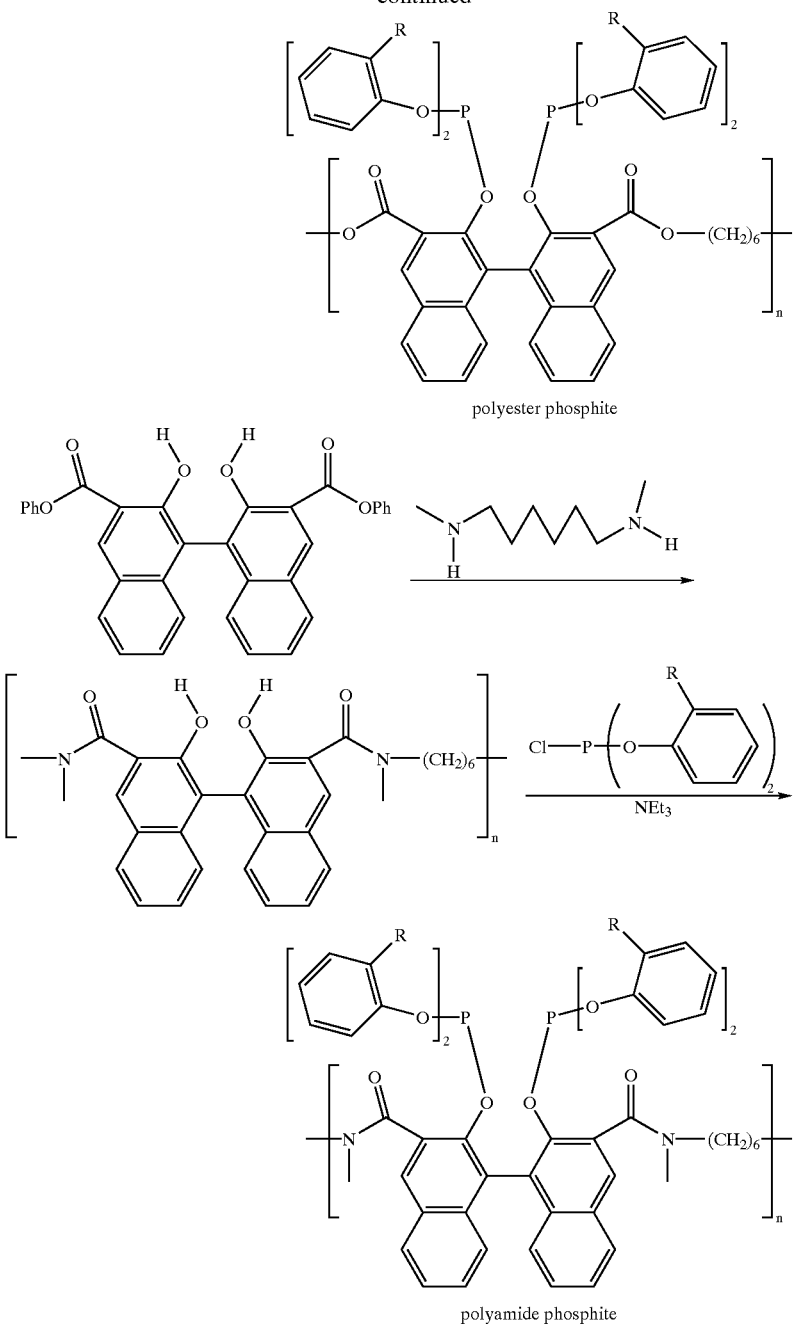

polyester phosphite polyamide phosphite

The molecular weight of the polymer depicted above can be adjusted according to need or desire by adjusting the conditions of the process or the moles of carbonyl compound, monomer, or both.

Polymer A can be combined with a Group VIII metal to produce a catalyst composition A. The term "metal" used herein refers to transition metal, transition metal compound, transition metal complex, or combinations thereof. The term "Group VIII" refers to the ACS version of the Periodic Table of the Elements, $67^{th}$ edition (1986–1987), CRC Handbook of Chemistry and Physics, Press, Boca Raton, Fla. For the catalyst composition, the polymer component is also referred to herein as a ligand.

Generally, a Group VIII metal is combined with a polymer disclosed above to produce the desired catalyst. Preferred Group VIII metals are rhodium, iridium, ruthenium, platinum, and combinations of two or more thereof. The most preferred is rhodium. The Group VIII metal is provided in the form of a compound, such as a hydride, halide, organic acid salt, ketonate, inorganic acid salt, oxide, carbonyl compound, amine compound, or combinations of two or more thereof. Preferred Group VIII metal compounds are $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, $[RhCl(COD)]_2$, and combinations of two or more thereof ("acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The rhodium compounds, suitable for hydroformylation, can be prepared or generated according to techniques well known in the art, as described, for example, in WO 95 30680, U.S. Pat. No. 3,907,847, and *J. Amer. Chem. Soc.*, 115, 2066, 1993. Rhodium compounds that contain ligands, which can be displaced by the present multidentate phosphite ligands, are a preferred source of rhodium. Examples of such preferred rhodium compounds are $Rh(CO)_2(acac)$, $Rh(CO)_2(C_4H_9COCHCO$-t-$C_4H_9)$, $Rh_2O_3$, $Rh_4(CO)_{12}$, $Rh_6(CO)_{16}$, $Rh(O_2CCH_3)_2$, Rh(2-ethylhexanoate), and combinations of two or more thereof.

The amount of transition metal can be any amount so long as favorable results can be obtained with respect to catalyst activity and process economy, when used as a catalyst. In general, the molar ratio of phosphorus ligand to transition metal generally can be from about 1:1 to about 100:1, preferably from about 1:1 to about 20:1 (moles phosphorus per mole metal).

Polymer B comprises repeat units derived from (1) phosphorus trichloride, (2) a second polyhydric alcohol, and (3) an aromatic diol. The $PCl_3$ can be blended with $Cl_2P(OAr^3)$ or $ClP(OAr^3)_2$ wherein $Ar_3$ is $C_6$ to $C_{24}$ aryl in which the aryl group can be substituted with alkyl, aryl, ether and ester.

The location of the OH groups is preferably placed such that the reaction with $PCl_3$ will not lead to predominate formation of monodentate phosphites.

Preferred second polyhydric alcohol has the formula selected from the group consisting of $(R^4)(HO)_m$—$Ar^2$—$A^1$—$Ar^2$—$(OH)_m(R^4)$, $(R^4)(HO)_m$—$Ar^2$—$(O$—$A^1)_p$—$O$—$Ar^2$—$(OH)_m(R^4)$, $(R^4)(OH)_m$—$Ar^2$—$Ar^2$—$(OH)_m(R^4)$, $(R^4)(OH)_m$—$Ar^2$—$A^2$—$Ar^2$—$(OH)_m(R^4)$, $(R^4)(HO)_m$—$Ar^2$—$A^1$—$C(O)$—$O$—$A^1$—$O$—$C(O)$—$A^1$—$Ar^2$—$(OH)_m$ $(R^4)$, $(R^4)(OH)_m$—$Ar^1$—$(OH)_m(R^4)$, and combinations thereof; when $R^4$ is not hydrogen and located ortho to the OH group, the other substituent ortho to the OH group is hydrogen;

- each $R^4$ is independently selected from the group consisting of hydrogen, $C_1$ to $C_{12}$ alkyl or cycloalkyl group, acetal, ketal, —$OR^3$, —$CO_2R^3$, $C_6$ to $C_{20}$ aryl group, —$SiR^3$, —$NO_2$, —$SO_3R^3$, —$S(O)R^3$, —$S(O)_2R^3$, —$CHO$, —$C(O)R^3$, F, Cl, —CN, or perhaloalkyl, —$C(O)N(R^3)(R^3)$, —$A^1Z$, and combinations of two or more thereof,
- each Z is —$CO_2R^3$, —$CHO$, —$C(O)R^3$, —$C(O)SR^3$, —$SR^3$, —$C(O)NR^1R^1$, —$OC(O)R^3$, —$OC(O)OR^3$, —$N$=$CR^1R^1$, —$C(R^1)$=$NR^1$, —$C(R^1)$=$N$—$O$—$R^1$, —$P(O)(OR^3)(OR^3)$, —$S(O)_2R^3$, —$S(O)R^3$, —$C(O)OC(O)R^3$, —$NR^3CO_2R^3$, —$NR^3C(O)NR^1R^1$, F, Cl, —$NO_2$, —$SO_3R^3$, —CN or combinations thereof;
- each $R^3$ is independently selected from the group consisting of $C_1$ to $C_{12}$ alkyl or cycloalkyl group, $C_6$ to $C_{20}$ aryl group.

When $R^4$ is independently selected from the group consisting of $C_1$ to $C_{12}$ alkyl or cycloalkyl group, acetal, ketal, —$OR^3$, —$CO_2R^3$, $C_6$ to $C_{20}$ aryl group, —$SiR^3$, —$SO_3R^3$, —$S(O)R^3$, —$S(O)_2R^3$, perhaloalkyl, —$C(O)N(R^3)(R^3)$, —$A^1CO_2R^3$, —$A^1OR^3$, the polyhydric alcohol can be $(OH)_m$ $Ar^1$—$R^4$—$R^4Ar^1(OH)_m$, $(OH)_mAr^1$—$R^4$—$A^1R^4Ar^1(OH)_m$, or combinations of two or more thereof.

All aryl groups, arylene groups, alkyl groups, alkylene groups, esters, ethers, acetals, and ketals disclosed in the invention can be substituted with one or more aryl groups, arylene groups, alkyl groups, alkylene groups, ethers, esters, acetals, and ketals.

Some representative second polyhydric alcohols include, but are not limited to, those shown in the following formulas.

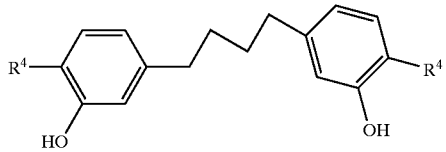

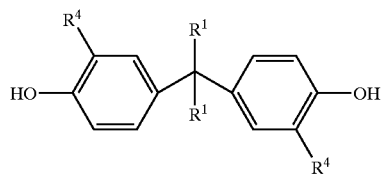

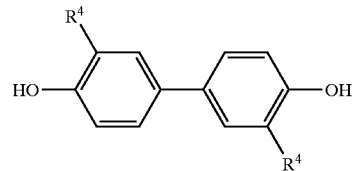

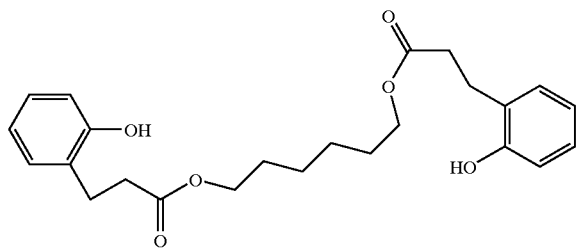

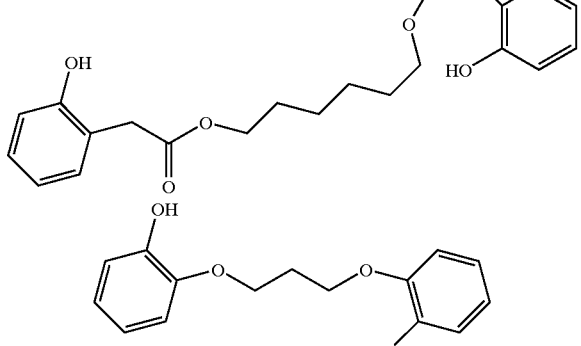

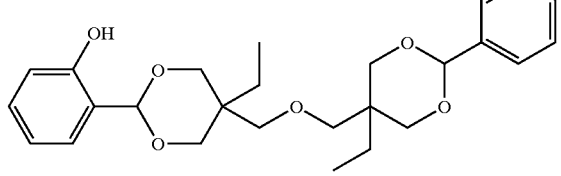

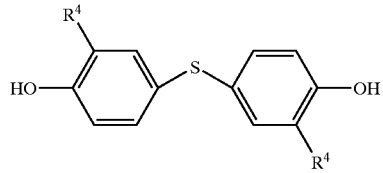

in which $R^1$ and $R^4$ are the same as disclosed above. The other positions on the aromatic ring, preferably para or meta to the oxygen atom, can also be substituted with alkyl, ether or ester groups.

Some representative examples are 6,6'-dihydroxy-4,4,4', 7,7,7'-hexamethyl bis-2,2'-spirochroman, 2,2'-diallylbisphenolA, bisphenol A, 4,4'-(1-methylethylidene) bis(2-(1-methylpropyl)phenol), 4,4,'-thiophenol, 4,4'-dihydroxydiphenylsulfone, 4,4'-sulfonylbis(2-methylphenol), bis(4-hydroxy-3-methylphenyl)sulfide, 2,2'-dis(4-hydroxy-3-methylphenyl)propane, 4,4,'-ethylidenebis(2,5-dimethylphenol), 4,4'-propylidenebis(2,5-dimethylphenol), 4,4'-benzylidenebis(2,5-dimethylphenol), 4,4'-ethylidenebis(2-isopropyl-5-methylphenol), and combinations of two or more thereof.

These second polyhydric alcohols can be produced by those skilled in the art. For example, the diacetal can be prepared by refluxing di(trimethstolpropane) with salicylaldehyde with oxalic acid as catalyst. For references for preparing acetal from acid catalyzed reaction of an aldehyde and an alcohol, see Tetrahedron, 1996, 14599; Tet Lett., 1989, 1609; Tetrahedron, 1990, 3315. 1,3-bis(2-hyroxyphenoxy)propane was prepared by a literature procedure, J. Org. Chem., 48, 1983,4867. 4,4'-ethylidenebis(2,5-dimethylphenol); 4,4'-propylidenebis(2,5-dimethylphenol); 4,4'-benzylidenebis(2,5-dimethylphenol); and 4,4'-ethylidenebis(2-isopropyl-5-methylphenol) can be prepared according to Bull. Chem. Soc. Jpn., 62, 3603 (1989).

In addition to the polyhydric alcohols shown above, compounds containing three or more phenolic groups can be used. Representative examples are shown below:

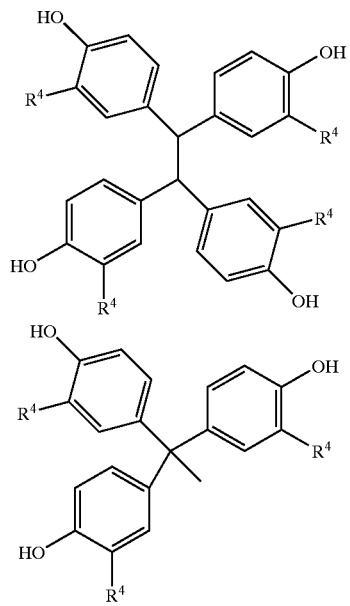

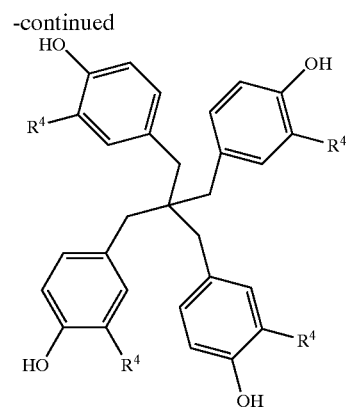

in which $R^4$ are the same as disclosed above. The other positions on the aromatic ring, preferably para or meta to the oxygen atom, can also be substituted with alkyl, ether or ester groups.

The aromatic diol has the following formula

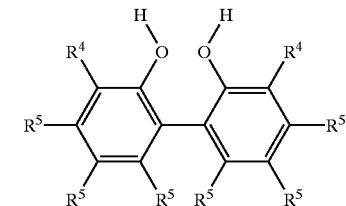

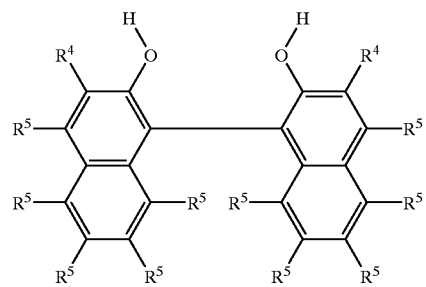

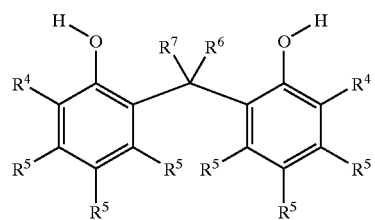

wherein:
each $R^4$ is independently selected from the group consisting of hydrogen, $C_1$ to $C_{12}$ alkyl or cycloalkyl group, acetal, ketal, $-OR^3$, $-CO_2R^3$, $C_6$ to $C_{20}$ aryl group, $-SiR^3$, $-NO_2$, $-SO_3R^3$, $-S(O)R^3$, $-S(O)_2R^3$, $-CHO$, $-C(O)R^3$, $-F$, $-Cl$, $-CN$, $-CF_3$, $-C(O)N(R^3)(R^3)$, $-A^1Z$, and combinations of two or more thereof;

Z is $-CO_2R^3$, $-CHO$, $-C(O)R^3$, $-C(O)SR^3$, $-SR^3$, $-C(O)NR^1R^1$, $-OC(O)R^3$, $-OC(O)OR^3$, $-N=CR^1R^1$, $-C(R^1)=NR^1$, $-C(R^1)=N-O-R^1$, $-P(O)(OR^3)(OR^3)$, $-S(O)_2R^3$, $-S(O)R^3$, $-C(O)OC(O)R^3$, $-NR^3CO_2R^3$, $-NR^3C(O)NR^1R^1$, F, Cl, $-NO_2$, $-SO_3R^3$, $-CN$, or combinations of two or more thereof;

each $R^3$ is independently selected from the group consisting of $C_1$ to $C_{12}$ alkyl or cycloalkyl group, $C_6$ to $C_{20}$ aryl group;

each $R^5$ independently is H, F, Cl, $C_1$ to $C_{12}$ alkyl or cycloalkyl, $C_6$ to $C_{20}$ aryl, —$OR^3$, —$CO_2R^3$, —$C(O)R^3$, —CHO, —CN, —$CF_3$, or combinations of two or more thereof;

each $R^6$ independently is H, $C_1$ to $C_{12}$ alkyl or cycloalkyl, $C_6$ to $C_{20}$ aryl, or combinations of two or more thereof; and each $R^7$ independently is H, $C_1$ to $C_{12}$ alkyl or cycloalkyl, $C_6$ to $C_{20}$ aryl, or combinations of two or more thereof.

These aromatic diols can be prepared by any means known to those skilled in the art. Examples include, but are not limited to, 2,2'-dihydroxy-3,3'-dimethoxy-5,5'-dimethyl-1,1'-biphenylene which can be prepared using the procedure described in *Phytochemistry*, 27, 1988, 3008; 2,2'-ethylidenebis(4,6-dimethylphenol) which can be prepared according to *Bull. Chem. Soc. Jpn.*, 1989, 62, 3603; 3,3'-dimethoxy-2,2'-dihydroxy-1,1'-binaphthalene which can be prepared by the procedure of *Recl. Trav. Chim. Pays. Bas.*, 1993, 112, 216; diphenyl 2,2'-dihydroxy-1,1'-binaphthalene-3,3'-dicarboxylate which can be prepared by the procedure described in *Tetrahedron Lett.*, 1990, 413; 3,3',5,5'-tetrmethyl-2,2'-biphenol and 3,3',4,4',6,6'-hexarnethyl-2,2'-biphenol which can be prepared using the procedure described in *J. Org. Chem.*, 1963, 28, 1063; and 3,3'-dimethyl-2,2'-dihydroxydiphenylmethane which can be prepared using the procedure described in *Synthesis*, 1981, 2, 143.

These aromatic diols can be incorporated in a polymer as in the polyester and polyamide described above for polymer A. These polymers containing the aromatic diols can be used in polymer B of the invention.

The solubilities of these polymeric phosphite ligands above generally depend on the molecular weight of the polymer and degree of branching. For soluble polymeric system, separation can therefore be done by extraction. With insoluble polymeric systems, the catalyst can be placed in fixed beds or separated by filtration from a reaction mixture. Alternatively, the solubility of the polymer can be adjusted to be soluble in the reactants and insoluble in the products. Thus, the reaction can be carried out homogeneously to obtain high conversion. The polymeric catalyst can then be separated by easy means such as decantation or filtration.

Polymer B can also form a catalyst composition B when combined with a catalytically active metal such as Group VIII metal. The metal can be the same as that above and the description of which is omitted herein for the interest of brevity.

It is presently preferred that polymer B is produced by a process which comprises (1) contacting phosphorus trichloride and a second polyhydric alcohol under a condition sufficient to produce a phosphorus-containing polymer and (2) contacting the phosphorus-containing polymer with an aromatic diol.

The definition and scope of the second polyhydric alcohol and aromatic diol are the same as those disclosed above.

In the first step of the process, a phosphorus-containing polymer with P—Cl bonds is prepared. The polymer containing phosphorochloridite can be prepared by treating one molar equivalent of $PCl_3$ with about two molar equivalent of reactive hydroxy groups in the second polyhydric alcohol in the absence of an organic base. The resulting solution is then treated with at least two equivalents of a base such as, for example, an organic base to produce a polymer containing phosphorochloridite. Suitable bases are organic amines disclosed above. The condition can include a temperature in the range of from about −40° C. to about 25° C., preferably about −20° C. to about 10° C., under a pressure that can accommodate the temperature, and for a sufficient period of time which can be about 1 minute to about 24 hours. The $PCl_3$ can be blended with $Cl_2P(OAr^3)$ and $ClP(OAr^3)_2$ wherein $Ar^3$ is a $C_6$ to $C_{24}$ aryl group in which the aryl group can be substituted with alkyl, aryl, ether and ester.

The molar ratio of phosphorus trichloride to the alcohol can be any ratio so long as the ratio is sufficient to effect the production of a desired phosphorus-containing polymer. With or without blending with $Cl_2P(OAr^3)$ and $ClP(OAr^3)_2$, generally the molar ratio of $PCl_3$ to reactive —OH groups can range from about 10:1 to about 1:3; preferably 1:2.

According to the invention, the phosphorus-containing polymer can be alternatively produced by contacting an N,N-dialkyl dichlorophosphoramidite with the second polyhydric alcohol to produce a polymeric phosphoramidite followed by contacting the polymeric phosphoramidite with an acid such as, for example, hydrochloric acid to produce the phosphorus-containing polymer such as, for example, polymeric phosphorochloridite. Generally any N,N-diallkyl dichlorophosphoramidite known to one skilled in the art can be used. Each of the alkyl group can contain 1 to about 20, preferably 1 to about 10 carbon atoms.

The molecular weight of the phosphorus-containing polymer can be modified by further contact with an aromatic diol that will react with unreacted P—Cl bonds. The contacting of the phosphorus-containing polymer with the aromatic diol can be carried out under a condition sufficient to produce a polymer containing a phosphite group. The contacting of the polymer containing phosphorochloridite with an aromatic diol can be carried out in the presence of a base disclosed above. Sufficient base can be used in steps (1) and (2) such that all generated HCl can be neutralized. The condition can include a temperature in the range of from about −50° C. to about 150° C., preferably about −40 C. to about 100° C., and most preferably, −30° C. to 80° C. under a pressure that can accommodate the temperature, and for a sufficient period of time which can be about 1 minute to about 24 hours.

The molar ratio of aromatic diol to unreacted P—Cl can be any ratio so long as the ratio is sufficient to effect the production of a desired phosphorus-containing polymer. The ratio generally can be in the range of from about 2:1 to about 1:2. It is most preferred that about equal mole of OH groups in the aromatic diol and the P—Cl bonds in the phosphorus-containing polymer be used.

The catalyst compositions A and B are useful for the hydroformylation of unsaturated organic compounds in which an aldehyde compound can be prepared.

The term "fluid" refers to liquid, gas, or combinations thereof. A fluid comprising hydrogen can contain about 1 to about 100% hydrogen. Similarly, a fluid comprising carbon monoxide can contain about 1 to about 100% CO. It is presently preferred that a 1:1 ratio of CO and hydrogen is used.

The reactant of the present process is an unsaturated organic compound preferably 2 to about 20 carbon atoms. Examples of suitable unsaturated organic compounds include, but are not limited to, linear terminal olefinic hydrocarbons, for example, ethylene, propylene, 1-butene, 1-pentene, 1-hexene, 1-octene, 1-nonene, 1-decene, 1-tetradecene, 1-hexadecene, 1-octadecene, 1-eicosene and 1-dodecene; branched terminal olefinic hydrocarbons, for example, isobutene and 2-methyl-1-butene; linear internal olefinic hydrocarbons, for example, cis- and trans-2-butene, cis- and trans-2-hexene, cis- and trans-2-octene, cis- and trans-3-octene; branched internal olefinic hydrocarbons, for example, 2,3-dimethyl-2-butene, 2-methyl-2-butene and 2-methyl-2-pentene; terminal olefinic hydrocarbons; internal olefinic hydrocarbon mixtures; for example, octenes, prepared by dimerization of butenes; cyclic olefins, for example, cyclohexene, cyclooctene; and combinations of two or more thereof.

Examples of suitable olefinic compounds also include those substituted with an unsaturated hydrocarbon group, including olefinic compounds containing an aromatic substituent such as styrene, alpha-methylstyrene and allylbenzene.

The unsaturated organic compound can also be substituted with one or more functional groups containing a heteroatom, such as oxygen, sulfur, nitrogen or phosphorus. Examples of these heteroatom-substituted ethylenically unsaturated organic compounds include vinyl methyl ether, methyl oleate, oleyl alcohol, 3-pentenenitrile, 4-pentenenitrile, 3-pentenoic acid, 4-pentenoic acid, methyl 3-pentenoate, 7-octen-1-al, acrylonitrile, acrylic acid esters, methyl acrylate, methacrylic acid esters, methyl methacrylate, acrolein, allyl alcohol, 3-pentenal, 4-pentenal, and combinations of two or more thereof.

The process of the invention can be illustrated as follow.

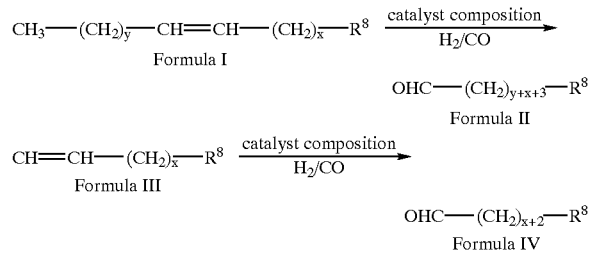

Wherein $R^8$ is H, —CN, —$CO_2R^1$, —$C(O)NR^1R^1$, —CHO, —$OR^3$, OH, or combinations of two or more thereof; y is an integer from 0 to 12; and x is an integer from 0 to 12. $R^1$ and $R^3$ are the same as those disclosed above Particularly preferred unsaturated organic compounds are 3-pentenenitrile, 3-pentenoic acid, 3-pentenal, allyl alcohol, and alkyl 3-pentenoate, such as methyl 3-pentenoate, and combinations of two or more thereof. The linear aldehyde compound prepared by the present process starting with one of these compounds can be used advantageously in the preparation of ε-caprolactam, hexamnethylenediamine, 6-aminocaproic acid, 6-aminocapronitrile or adipic acid, which are precursors for Nylon-6 and/or Nylon-6,6.

The process of the invention also can be carried out with a mixture that comprises two or more unsaturated organic compounds. For example, 3-pentenenitrile can be present in a mixture containing 4-pentenenitrile. Because the 4-isomer reacts in a similar fashion as the corresponding 3-isomer to the desired linear aldehyde, a mixture of isomers can be used directly in the present process.

The 3-pentenenitrile may be present in mixtures containing impurities that do not interfere with the hydroformylation reaction. An example is 2-pentenenitrile.

The hydroformylation process according to the invention can be performed as described below.

The process of the invention can be carried out by any means known to one skilled in the art such as, for example, the one disclosed in U.S. Pat. No. 4,769,498, disclosure of which is incorporated herein by reference. Generally, the process can be carried out under any condition sufficient to effect the production of a desired aldehyde. For example, the temperature can be from about 0° C. to 200° C., preferably from about 50 to 150° C., and more preferably from 85° to 110° C. The pressure may vary from normal pressure to 5 MPa, preferably from 0.1 to 2 MPa. The pressure is, as a rule, can also be equal to the combined hydrogen and carbon monoxide partial pressures. However, extra inert gases may also be present; the pressure may vary from normal pressure to 15 MPa when inert gases are present. The molar ratio of hydrogen to carbon monoxide is generally between 10:1 and 1:10, and preferably between 6:1 and 1:2.

The amount of transition metal compound is selected so that favorable results can be obtained with respect to catalyst activity and process economy. In general, the concentration of transition metal in the reaction medium, which comprises an unsaturated organic compound, a catalyst composition, and solvent (if present), can be between 10 and 10,000 ppm and more preferably between 50 and 1000 ppm, calculated as free metal.

The molar ratio of the ligand to Group VIII metal is selected so that favorable results can be obtained with respect to catalyst activity and desired aldehdye selectivity. This ratio generally is from about 1 to 100 and preferably from 1 to 20 (moles phosphorus per mole metal).

The solvent may be the mixture of reactants of the hydroformrnylation reaction itself, such as the starting unsaturated compound, the aldehyde product and/or by-products. Other suitable solvents include saturated hydrocarbons (for example, kerosene, mineral oil, or cyclohexane), ethers (for example, diphenyl ether or tetrahydrofuiran), ketones (for example, acetone, cyclohexanone), nitrites (for example, acetonitrile, adiponitrile or benzonitrile), aromatics (for example, toluene, benzene, or xylene), esters (for example, methyl valerate, caprolactone), Texanol® (Union Carbide), dimethylformamide, or combinations of two or more thereof.

The hydroformylation process can be run in solution or in the gas phase.

When the hydroformylation is carried out in the vapor (gas) phase, the preferred temperature range is from about 50° C. to about 180° C., most preferably from about 90° C. to 110° C. The temperature must be chosen so as to maintain all of the reactants and products in the vapor phase, but low enough to prevent deterioration of the catalyst. The particular preferred temperature depends to some extent on the catalyst being used, the olefinic compound being used, and the desired reaction rate. The operating pressure is not particularly critical and can conveniently by from about 0.101 to 1.01 MPa. The pressure and temperature combination must be chosen so as to maintain reactants and products in the vapor phase. A given catalyst is loaded into a reactor, such as a tubular reactor, taking care to avoid exposure of air-sensitive catalysts to $O_2$ from the air. A gaseous mixture of the desired olefinic compound, CO and $H_2$, along with any desired diluent, such as $N_2$, He or Ar, is then passed through the reactor while contacting the catalyst. The reaction products are generally liquid at room temperature and are conveniently recovered by cooling. The reactor effluent can be directly connected to a sampling valve and can be analyzed by gas chromatography. Aldehydic products, such as linear and branched butyraldehydes obtained from hydroformylation of propylene, can be quantitatively separated and analyzed using a 30 M DB-Wax® capillary GC column.

EXAMPLES

The following non-limiting, representative examples illustrate the process and catalyst compositions of this invention. All percentages are on a mole basis, unless otherwise noted. For all the examples described below, the unit formula weight of the polymers were determined based on the expected formula.

Example 1

Preparation of Polyester Derived Polymeric Phosphite Containing o-cresol as Terminal Groups Preparation of Polyester A catalyst solution was prepared by warming 0.1 g Fascat 4102 (butyltin tris(2-ethylhexanoate)) and 10 g of 1,6-hexanediol on the hot plate in a small vial with a small magnet. The solution was kept warm. A mixture containing 5 g of dimethyl 2,2'-dihydroxy-1,1'-binaphthalene-3,3'-dicarboxylate (0.0123 mmoles; reference for preparation; see *J. Am. Chem. Soc.,* 1954, 76,296 and *Tetrahedron Let.,* 1990, 413), 2.6 g of 1,6-bexanediol and 1.75 g of warm catalyst solution was placed in a 25 ml microware 1-neck rb (round bottom) flask connected to a distillation head and receiver with a precalibrated heating mantle while stirring magnetically until methanol started to distill off (the temperature was about 180° C. at which temperature the dimethyl 2,2'-dihydroxy-1,1'-binaphthalene-3,3'-dicarboxylate had all dissolved). The temperature was then increased until the 1,6-hexanediol started to reflux in the top of the flask (220° C.). The mixture was allowed to reflux for about an hour and then house vacuum was gradually applied. Full pump vacuum was then applied to distill off the excess 1,6-hexanediol. The pressure was lowered very slowly to 4 mm Hg over the next two hours in order to avoid bumping. The reaction mixture was then polymerized at 270° C. for 2 hours while distilling off most of the 1,6-hexanediol. After cooling, the reaction mixture was refluxed with 25 ml of acetone for three hours and then cooled and filtered. $^1$H nmr spectrum indicated degree of polymerization to be 6.

Preparation of Polyester 1

The polymer prepared in example 1 was added to the phosphorchloridite of o-cresol in the presence of triethylamine in toluene. The mixture was stirred overnight and then filtered. The solvent was removed to give the desired polymer. $^{31}$P{H} (121.4 MHz, CDCl$_3$): 132.13, 131.7, 130.6, 130.5, 130.4, 127.6 ppm.

Example 1A

Hydroformylation of 3-Pentenenitrile with Polyester 1

A stock solution was prepared by mixing 0.203 g of Rh(CO)$_2$(acac), 32.4 g of 3-pentenenitrile, 4.0 g of 1,2-dichlorobenzene as internal standard in toluene (total volume: 400 ml). A portion of this solution was added to a glass-lined pressure vessel containing approximately 2.5 equivalents of bidentate phosphite to rhodium with polyester . The reactor was sealed, pressurized to 0.52: MPa 1:1CO/H$_2$ and heated at 95° C. for 3 hours. GC analysis: 91% conversion of 3-pentenenitrile; linearity of aldehydes produced: 47%; selectivity to 5-formylvaleronitrile: 38%.

Example 1B

Hydroformylation of 3-Pentenenitrile with Polyester 1

A solution containing 3-pentenenitrile (0.5 M), Rh(CO)$_2$(acac) (0.9 mM), and 1,2-dichlorobenzene (internal standard, 0.14 M) in toluene was prepared in a drybox. A portion of this solution was added to a glass-lined pressure vessel and enough of a 0.05 M solution of polyester1 was added to give 2 equivalents of bidentate phosphite to Rh. The reactor was sealed, pressurized to 0.45 MPa 1:1CO/H$_2$ and heated to 95° C. for 3 hours. The reactor was cooled and depressuized and a sample of the reaction mixture was analyzed by gas chromatography. GC analysis (mole%) 2-pentenenitrile 2.5%, valeronitrile 20.3%, 3-pentenenitrile 11.5%, 5-formylvaleronitrile 58.8%. 91% conversion of 3-pentenenitrile; linearity of aldehydes produced: 56%; selectivity to 5-formylvaleronitrile: 44%.

Example 1C

Undecene Hydroformylation with Polyester 1

A solution containing undecene (0.5 M), Rh(CO)$_2$(acac) (9 mM), and 1,2-dichlorobenzene (internal standard, 0.26 M) in toluene was prepared in a drybox. A portion of this solution was added to a glass-lined pressure vessel containing approximately 5.5 equivalents of bidentate phosphite to rhodium with polyester1. The reactor was sealed, pressurized to 0.45 MPa psi 1:1CO/H$_2$ and heated to 95° C. for 3 hours. The reactor was cooled and depressuized and a sample of the reaction mixture was analyzed by gas chromatography on an HP 6890 Chromatograph with a DB-WAX phase fused silica capillary column (30 meters, 0.32 mm I.D., 0.25 um film thickness) purchased from JW Scientific. GC analysis(wt %): undecane, 1%; 1-undecene, 5%; internal undecenes 23%, methyl undecanal, 0%; dodecanal 71%.

Example 1D

Hydroformylation of Methyl 3-Pentenoate Results with Polyester 1

In a drybox a solution containing methyl-3-pentenoate (0.5 M), Rh(acac)(CO)$_2$ (1.0 mM), and 1,2-dichlorobenzene (internal standard, 0.14 M) in toluene was prepared. A portion of this solution was added to a glass-lined pressure vessel and enough of a solution of polyester1 (0.05 M) was added to give 4.6 equivalents of bidentate phosphite to Rh. The reactor was sealed, pressurized to 0.45 MPa with 1:1CO/H$_2$ and heated to 95° C. for 3 hours. The reactor was cooled and depressuized and a sample of the reaction mixture was analyzed by gas chromatography on an HP 5890A Chromatograph with a DB-FFAP fuised silica capillary column (30 meters, 0.32 mm I.D., 0.25 um film thickness) purchased from JW Scientific. GC analysis: 41% conversion of methyl 3-pentenoate; linearity of aldehydes produced: 93%; selectivity to methyl 5-formylvalerate: 78%.

Example 2

Preparation of Polyester 2

Same procedure as with example 1 except the phosphochloridite of the acetal containing phenol derived from the reaction of salicylaldehyde and 1,3-propanediol was used. $^{31}$P{H} (121.4 MHz, CDCl$_3$): major resonance at 129.8 ppm, other resonances at 147.5, 147.2, 133.4, 131.1, 130.5, 130.2, 130.0, 129.4 ppm.

Example 2A

Hydroformylation of 3-Pentenenitrile with Polyester 2

A 100 ml autoclave was charged with 0.8 g of polyester2. The autoclave was evacuated and a solution containing 0.04 g of $Rh(CO)_2(acac)$, 2 g of 1,2-dichlorobenzene and 70 g of 3-pentenenitrile was loaded under vacuum. The autoclave was pressurized with 0.45 Mpa psi $CO/H_2(1:1)$, heated at 95° C. under vigorous stirring for 6 hours while flowing $CO/H_2$ at a rate of 20 mumin for 6 hours. A sample was removed from the reactor after 6 hours and analyzed by GC (mole %): 2-pentenenitrile 0.3%, valeronitrile 10.3%, 3-pentenenitrile 0.8%, 5-formylvaleronitrile 82%. 99% conversion of 3-pentenenitrile; linearity of aldehydes produced: 92.6%; selectivity to 5-formylvaleronitrile: 83.3%.

Example 2B

Hydroformylation of 3-Pentenenitrile with Polyester 2

This reaction was run as in Example 1B with the modification that approximately 5 equivalents of bidentate phosphite to Rh were used with polyester 2. GC analysis: 97% conversion of 3-pentenenitrile; linearity of aldehydes produced: 92%; selectivity to 5-formylvaleronitrile: 72%.

Example 2C

Hydroformylation of Methyl 3-Pentenoate with Polyester 2

This reaction was run as in Example 1D with the modification that 4.6 equivalents of bidentate phosphite to Rh were used with polyester2. GC analysis: 84% conversion of methyl 3-pentenoate; linearity of aldehydes produced: 99%; selectivity to methyl 5-formylvalerate: 87%.

Example 3

Preparation of Polyester 3

Same procedure as with example 1except the phosphochloridite of β-naphthol was used. $^{31}P\{H\}$ (202 MHz, $CDCl_3$): major resonance at 129.98 ppm with minor ones at 145.9, 131.3, 130.1, 129.8, 129.2 ppm.

Example 3A

Hydroformylation of 3-Pentenenitrile Using Polyester 3

This reaction was run as in Example 1B with the modification that approximately 5 equivalents of bidentate phosphite to Rh were used with polyester 3. GC analysis: conversion: 97% conversion of 3-pentenenitrile; linearity of aldehydes produced: 80%; selectivity to 5-formylvaleronitrile: 66%.

Example 3B

Hydroformylation of Undecene Using Polyester 3

In a drybox a solution containing undecene (0.5 M), $Rh(CO)_2(acac)$ (9 mM), and 1,2-dichlorobenzene (internal standard, 0.26 M) in toluene was prepared. A portion of this solution was added to a glass-lined pressure vessel containing approximately 5.5 equivalents of bidentate phosphite to rhodium with polyester3. The reactor was sealed, pressurized to 0.45 Mpa $1:1CO/H_2$ and heated to 95° C. for 3 hours. The reactor was cooled and depressuized and a sample of the reaction mixture was analyzed by gas chromotography on an HP 6890 Chromatograph with a DB-WAX phase fused silica capillary column (30 meters, 0.32 mm I.D., 0.25 um film thickness) purchased from JW Scientific. GC analysis (wt %): undecane, 0.7%; 1-undecene, 3.6%; internal undecenes 36.9%, methyl undecanal, 0.4%; dodecanal 58.3%.

Example 3C

Hydroformylation of Methyl 3-Pentenoate Using Polyester 3

This reaction was run as in Example 1D with the modification that 4.6 equivalents of bidentate phosphite to Rh were used with polyester3. GC analysis: 56% conversion of methyl 3-pentenoate; linearity of aldehydes produced: 97%; selectivity to methyl 5-formylvalerate: 79%.

Example 4

Preparation of Polyamide 1

Preparation of Polyamide

1. A 75-cc stainless steel autoclave equipped with a glass sleeve was charged with 3.05 g (21 mmol) N,N'-dimethyl-1,6-hexanediamine, 30 g deionized water, and 10.9 g (21 mmol) diphenyl 2,2'-dihydroxy-1,1'-binaphthalene-3,3'-dicarboxylate. The reactor contents were purged with nitrogen.

2. The reactor was set to vent at 250 psig. The reactor was heated to 200° C. over forty minutes, then heated to 240° C. over sixty minutes. At 100 minutes, the reactor pressure was reduced to atmospheric pressure over 60 minutes while temperature was increased to 275° C. The reactor was held at one atmosphere steam and 275° C. for forty-five minutes.

3. After cooling, the solid product, 10 g, was removed.

Preparation of Polyamide 1

The polyamide from above was reacted with the phosphochloridite of o-cresol in toluene with triethylamine as the base. The mixture was filtered and the solvent removed by rotary evaporation to give the desired polymeric phosphite. The polymer was soluble in chloroform. $31P\{H\}$ (202 MHz, $CDCl_3$): major resonance at 132.1 ppm.

Example 4A

Hydroformylation of 3-Pentenenitrile with Polyamide 1

This reaction was run as in Example 1B with the modification that approximately 6 equivalents of bidentate phosphite to Rh were used with polyamide 1. GC analysis: 86% conversion of 3-pentenenitrile; linearity of aldehydes produced: 40%; selectivity to 5-formylvaleronitrile: 35%.

Example 4B

Hydroformylation of Methyl 3-Pentenoate with Polyamide 1

In a drybox a solution containing methyl-3-pentenoate (0.49 M), $Rh(CO)—_2(acac)$ (8.6 mM), and 1,2-dichlorobenzene (internal standard, 0.14 M) in tetrahydrofuran was prepared. A portion of this solution was added to a glass-lined pressure vessel containing approximately 2.4 equivalents of bidentate phosphite to rhodium with polyamide1. The reactor was sealed, pressurized to 0.45 MPa with $1:1CO/H_2$ and heated to 95° C. for 3 hours. The reactor was cooled and depressuized and a sample of the reaction mixture was analyzed by gas chromatography on an HP 5890A Chromatograph with a DB-FFAP fused silica capillary column (30 meters, 0.32 mm I.D., 0.25 um film thickness) purchased from JW Scientific. GC analysis: 62% conversion of methyl 3-pentenoate; linearity of aldehydes produced: 34%; selectivity to methyl 5-formylvalerate: 28%.

Example 5

Preparation of Branched Polymer 1

Preparation of Diol

Reaction of 3-(2-hydroxyphenyl)propionic acid with 1,6-hexanediol. In a 100 ml rb flask was charged 16.447 g (0.099 mole) of 3-(2-hydroxyphenyl)propionic acid, 20 mg of Fascat 4102 and 5.840 g (0.049 mole) of 1,6-hexanediol. The mixture was heated at 170–225° C. for three hours to remove water. The mixture was then heated at 275° C. for 70 minutes and then the temperature was lowered to 200° C. House vacuum was applied and the temperature increased to 260° C. for 20 minutes. The mixture was flash column chromatographed using 20% ethyl acetate/hexane as eluent. Thus obtained was 9.95 g of the desired product as an oil. $^1$H nmr (500 Mhz, $CDCl_3$): 7.2 (br s, 2H), 6.95 (m, 4H), 6.7 (m, 4H), 3.9 (t, 4H), 2.85 (t, 4H), 2.6 (t, 4H), 1.45 (m, 4H), 1.2 (m, 4H).

Preparation of Branched Polymer 1

Under an inert atmosphere, a 100 ml rb flask with a magnetic stirrer was charged with 0.900 g of phosphorus trichloride, 2.716 g of the diol from above and 10 ml of toluene. The mixture was cooled at –30° C. and a pre-cooled solution of tri-n-butylamine in 20 ml (–30° C.) of toluene was added over a 15 minute period. $^{31}$P{H} (202 Mhz) of the reaction mixture indicated a major resonance at 162 ppm. To this mixture was added 1.725 g of diphenyl-2,2'-dihydroxy-1,1'-binaphthalene-3,3'-dicarboxylate (prepared analogously to the methyl ester derviative; see *J. Am. Chem. Soc.*, 1954, 76,296 and *Tetrahedron Lett.*, 1990, 413) and additional 2.0 g of tri-n-butylamine. The gel was allowed to stand overnight. Some solvent was removed and acetonitrile was added. The yellow solid (5.610 g) was collected. Solid state $^{31}$P magic-angle-spinning NMR (121.5 Mhz): 143 and 125 ppm. This polymer was not soluble in $CDCl_3$.

Example 5A

Hydroformylation of 3-Pentenenitrile with Branched Polymer 1

In a drybox, a solution containing 3-pentenenitrile (0.5 M), $Rh(CO)_2(acac)$ (9 mM), and 1,2-dichlorobenzene (internal standard, 0.14 M) in tetrahydrofuran was prepared. A portion of this solution was added to a glass-lined pressure vessel containing approximately 3 equivalents of bidentate phosphite to rhodium were used with branched polymer1. The reactor was sealed, pressurized to 65 psi 1:1CO/$H_2$ and heated to 95° C. for 3 hours. The reactor was cooled and depressurized and a sample of the reaction mixture was analyzed by gas chromatography. GC analysis: 94% conversion; selectivity to 5-formylvaleronitrile: 67% on a mole basis; linearity of aldehydes produced: 82%. GC analysis: (mole %) 2-pentenenitrile 0.2%, valeronitrile 17.5%, 3-pentenenitrile 5.7%, 5-formylvaleronitrile 63.2%. 94% conversion of 3-pentenenitrile; linearity of aldehydes produced: 82%; selectivity to 5-formylvaleronitrile: 67%.

Example 5B

Hydroforrnylation of 3-Pentenenitrile with Branched Polymer 1

A 100 ml autoclave was charged with 0.9 g of branched polymer1. The autoclave was evacuated and a solution containing 0.039 g of $Rh(CO)_2(acac)$, 2 g of 1,2-dichlorobenzene and 70 g of 3-pentenenitrile was loaded under vacuum. The autoclave was pressurized with 0.45 MPa CO/$H_2$(1:1), heated at 95 C. under vigorous stirring for 6 hours while flowing CO/$H_2$ at a rate of 20 ml/min for 6 hours. A sample was removed from the reactor after 6 hours and analyzed by GC (mole %):2-pentenenitrile 2.1%, valeronitrile 12.4%, 3-pentenenitrile 5.2%, 5-formylvaleronitrile 68.5%. 95% conversion of 3-pentenenitrile; linearity of aldehydes produced: 86%; selectivity to 5-formylvaleronitrile: 74%.

Example 5C

Hydroformylation of Methyl 3-Pentenoate with Branched Polymer 1

This reaction was run as in Example 4B with the modification that 1.6 equivalents of bidentate phosphite to Rh were used with branched polymer1. GC analysis: 97% conversion of methyl 3-pentenoate; linearity of aldehydes produced: 91%; selectivity to methyl 5-formylvalerate: 82%.

Example 6

Branched Polymer 2

Under an inert atmosphere, a 250 ml rb flask with a magnetic stirrer was charged with 0.412 g of phosphorus trichloride, 1.105 g of 6,6'-dihydroxy-4,4,7,7-hexamethyl bis-2,2-spirochroman in 20 ml THF and 20 ml of toluene. The mixture was cooled to –30° C. and a precooled solution (–30° C.) of triethylamine (0.800 g) in 20 ml of toluene. The slurry was stirred for 1.5 hours. $^{31}$P{H} (202 MHz) of the reaction mixture indicated a major resonance at 1:61.8 and 161.7 ppm. To this mixture was added 0.790 g of diphenyl-2,2'-dihydroxy-1,1'-binaphthalene-3,3'-dicarboxylate and additional 0.700 g of triethylarnine. The mixture was stirred overnight and then filtered, washed with tetrahydrofuran. The solvent was removed by rotary evaporation to give 2.124 g of yellow solid. $^{31}$P {H} nmr (202.4 MHz, $CDCl_3$): major peak at 133.0 ppm.

Example 6A

Hydroformylation of 3-Pentenenitrile with Branched Polymer 2

Reaction was run as in example 5A but with 1.5 equivalent of bidentate phosphite to Rh with branched polymer2. GC analysis: (mole %) 2-pentenenitrile 1.0%, valeronitrile 12.6%, 3-pentenenitrile 4.2%, 5-formylvaleronitrile 27.4%. 96% conversion of 3-pentenenitrile; linearity of aldehydes produced: 33%; selectivity to 5-formylvaleronitrile: 29%.

Example 6B

Hydroformylation of 3-Pentenenitrile with Branched Polymer 2

In a drybox, a solution containing 3-pentenenitrile (0.5 M), of $Rh(CO)-_2(acac)$ (8.3 mM), and 1,2-dichlorobenzene (internal standard, 0.14 M) in tetrahydrofuran was prepared. A portion of this solution was added to a glass-lined pressure vessel containing approximately 3 equivalents of bidentate phosphite to rhodium with branched polymer2. The reactor was sealed, pressurized to 0.45 MPa 1:1CO/$H_2$ and heated to 95° C. for 3 hours. The reactor was cooled and depressuized and a sample of the reaction mixture was analyzed by gas chromotography. GC analysis: (mole %) valeronitrile 14.8%, 3-pentenenitrile; 1.8%, 5-formylvaleronitrile 51.5%. 98% conversion of 3-pentenenitrile; linearity of aldehydes produced: 62%; selectivity to 5-formylvaleronitrile: 52%.

Example 7

Preparation of Polymer 3

Preparation of Diol Derived from Di(trimethylolpropane) and Salicylaldehyde

To a rb flask equipped with a Dean Stark condenser were added 11.12 g of di(trimethylolpropane), 10.85 g of salicylaldehyde, 300 ml of toluene and 1.5 g of oxalic acid. The mixture was refluxed for 16 hr. The mixture was cooled, washed with water, brine, and dried over sodium sulfate. The solvent was removed and the oil was dissolved in a minimum amount of ether. Hexane was added to precipitate out the desired product. 3.2 g of white solid was collected. APCI MS (atmospheric pressure chemical ionization mas spectroscopy): calculated for $C_{26}H_{34}O_7$: 458.55; found: 459.2.

Preparation of Polymer 3

Polymer3 was prepared similar to example 5 except the diol from above was used. The diol from above was reacted with $PCl_3$ and then the resultant phosphorochloridite solution was reacted with diphenyl-2,2'-dihydroxy-1,1'-, binaphthalene-3,3'-dicarboxylate. Triethylamine was used as the base. $^{31}P$ {H} nmr (202.4 MHz, $CDCl_3$): sharp resonance at 145.6 and a broad resonance at 135.4 ppm.

Example 7A

Hydroformylation of 3-Pentenenitrile with Polymer 3

A 100 ml autoclave was charged with 0.9 g of polymer3. The autoclave was evacuated and a solution containing 0.035 g of $Rh(CO)_2(acac)$, 2 g of 1,2-dichlorobenzene and 70 g of 3-pentenenitrile was loaded under vacuum. The autoclave was pressurized with 0.45 MPa CO/H2(1:1), heated at 95° C. under vigorous stirring for 6 hours while flowing $CO/H_2$ at a rate of 20 ml/min for 6 hours. A sample was removed from the reactor after 6 hours and analyzed by GC (mole %) 2-pentenenitrile, 2%, valeronitrile 13%, 3-pentenenitrile 10%, 5-formylvaleronitrile 69%. 89.4% conversion of 3-pentenenitrile; linearity of aldehydes produced: 94%; selectivity to 5-formylvaleronitrile: 79%. A 5 gr sample was taken from the autoclave after 6 hours. The solution was completely homogeneous. Upon standing a white precipitate formed.

Example 7B

Hydroformylation of 3-Pentenenitrile with Polymer 3

Reaction was run as in example 5A but with 3 equivalent of bidentate phosphite to Rh with polymer3. GC analysis: 98% conversion of 3-pentenenitrile; linearity of aldehydes produced: 95%; selectivity to 5-formylvaleronitrile: 81%.

Example 7C

Hydroformylation of Methyl 3-Pentenoate with Polymer 3

This reaction was run as in Example 4B with the modification that 4.9 equivalents of bidentate phosphite to Rh with polymer3 were used. GC analysis: 96% conversion of methyl 3-pentenoate; linearity of aldehydes produced: 99%; selectivity to methyl 5-formylvalerate: 87%.

Example 8

Preparation of Branched Polymer 3

The reaction was similar to example 6 except the diol from example 7 was used. The diol from example 7 was reacted with $PCl_3$ and then the resultant phosphorochloridite solution was reacted with diphenyl-2,2'-dihydroxy-1,1'-binaphthalene-3,3'-dicarboxylate. Tri-n-butylamine was used as the base. The polymer was not soluble in $CDCl_3$.

Example 8A

Hydroformylation of 1-Octene with Branched Polymer 3

A mixture of $Rh(CO)2(acac)$(3 mg,0.012 mmole), branched polymer3 (insoluble) (26 mg), 1-Octene (98 mg,0.9 mmole), and THF(0.5 ml) was heated at 80 C. under 100 psi of $CO/H_2(1/1)$ for 1 hr. Butyl ether(2.6 mg, 0.02 mmole) was added into the mixture as the internal standard and the mixture was analyzed by Gas Chromatograph with Chrompack CP-SIL 8 column(30 m×0.32 mm ID). 98.8% Conversion was obtained with 40.8 wt % of Nonyl aldehyde, 1.3 wt % of 2-Methyl-1-octanal, 6.2 wt % of Octane, and 29.0 wt % of Octene isomers.

Example 8B

Hydroformylation of 3-Pentenenitrile with Branched Polymer 3

This is an example of an insoluble catalyst. A 100 ml autoclave was charged with 0.9 g of branched polymer3. The autoclave was evacuated and a solution containing 0.035 g of $Rh(CO)_2(acac)$, 2 g of 1,2-dichlorobenzene and 70 g of 3-pentenenitrile was loaded under vacuum. The autoclave was pressurized with 0.45 MPa $CO/H_2(1:1)$, heated at 95° C. under vigorous stirring for 6 hours while flowing $CO/H_2$ at a rate of 20 ml/min for 6 hours. A sample was removed from the reactor after 6 hours and analyzed by GC (mole %): 2-pentenenitrile, 2.4%, valeronitrile 16%, 3-pentenenitrile 8%, 5-formylvaleronitrile 67.4%. 92% conversion of 3-pentenenitrile; linearity of aldehydes produced: 94%; selectivity to 5-formylvaleronitrile: 75.5%.

Example 8C

Hydroformylation of Methyl-3-Pentenoate with Branched Polymer 3

This reaction was run as in Example 4B with the modification that 2.3 equivalents of bidentate phosphite to Rh with branched polymer 3 were used. GC analysis: 96% conversion of methyl 3-pentenoate; linearity of aldehydes produced: 91%; selectivity to methyl 5-formylvalerate: 76%.

Example 9

Preparation of Branched Polymer 4

Branched polymer4 was prepared similar to example 6 except the 2,2-bis(4-hydroxy-3-methylphenyl)propane was used as the diol to prepare the phosphorochloridite. The resultant phosphorochloridite solution was reacted with 3,3', 5,5'-tetramethyl-2,2'-biphenol to make the branched polymer. N N-Diisopropylethylamine was used as the base. The polymer was not soluble in CDCl$_3$.

Preparation of Rh Catalyst from Branched Polymer 4

0.430 g of the branched polymer4 and 456 mg of Rh(CO)2(acac) were mixed in 10 ml of THF and the insoluble catalyst was filtered, washed with THF and vacuum dried.

Example 9A

Hydroformylation of Propylene in the Gas Phase with Rh Catalyst Derived from Branched Polymer 4

An empty 0.25-inch (0.64 cm) diameter, 15-inch (37.5 cm) long stainless steel tubular reactor was placed in a nitrogen-filled glove box. A plug of glass wool was placed in the bottom end of the reactor, followed by 0.47 g of the catalyst from above. A thermocouple was inserted into the top of the reactor. Both ends of the reactor were sealed with metal fittings, and the reactor was removed from the glove box and was connected to stainless steel reactor feed lines purged with nitrogen. The reactor was equipped with a by-pass line to allow for a flow of CO and H$_2$ to be established before opening the inlet side of the reactor to the feed gases. The desired temperature of 100° C. was established in the reactor by means of a split tube furnace surrounding the reactor. When the desired temperature and flow rates of CO and H$_2$ feed gases had been achieved, a valve was turned to begin passing CO and H$_2$ over the catalyst. Periodically, reactor effluent samples were analyzed by gas chromatography for the amounts of unreacted propylene, linear and branched butyraldehyde. The run was at 100° C. and at a total pressure of 0.69 MPa. Propylene/CO/H2=2/2/2 cc/min. After a total of 93 hr, the average linear/branch ratio (n-butyraldehyde/isobutyraldehyde) was ~7.3, with an average propylene conversion of ~65%.

Example 10

Preparation of Branched Polymer 5

Branched polymerS was prepared similar to example 6 except the 2,2-diallylbisphenol A was used as the diol to prepare the phosphorochloridite. The resultant phosphorochloridite solution was reacted with diphenyl-2,2'-dihydroxy-1,1'-binaphthalene-3,3'-dicarboxylate to make the branched polymer. N,N-Diisopropylethylamine was used as the base. The polymer was not soluble in CDCl$_3$.

Preparation of Rh Catalyst from Branched Polymer 5

0.494 g of the branched polymer5 and 456 mg of Rh(CO)2(acac) were mixed in 10 ml of THF and the insoluble catalyst was filtered, washed with THF and vacuum dried.

Example 10A

Hydroformylation of Propylene in the Gas Phase with Rh Catalyst Derived from Branched Polymer 5

The reaction was carried out as in example 9A except 0.36 g of the above Rh catalyst was used. Propylene/CO/H2=2/2/2 cc/min. After a total of 46 hr, the average linear/branch ratio (n-butyraldehyde/isobutyraldehyde) was about 20, with an average propylene conversion of ~60%.

Example 10B

Hydroformylation of 3-Pentenenitrile Using Branched Polymer 5

Reaction was run as in example 5A but with 2 equivalent of bidentate phosphite to Rh with branched polymer5. GC analysis: 92% conversion of 3-pentenenitrile; linearity of aldehydes produced: 68%; selectivity to 5-formylvaleronitrile: 51%.

Example 11

Preparation of Branched Polymer 6

Branched polymer6 was prepared similar to example 6 except 6,6-dihydroxy-4,4,4',7,7,7'-hexamethylbis-2,2'-spirochroman was used as the diol to prepare the phosphorochloridite. The resultant phosphorochloridite solution was reacted with 2,2'-binaphthol to make the branched polymer. Tri-n-butylamine was used as the base. The polymer was not soluble in CDCl$_3$.

Preparation of Rh Catalyst from Branched Polymer 6

0.487 g of the branched polymer6 and 0.456 g of Rh(CO)$_2$(acac) were mixed in 10 ml of THF and the insoluble catalyst was filtered, washed with THF and vacuum dried.

Example 11A

Hydroformylation of Propylene in the Gas Phase with Rh Catalyst Derived from Branched Polymer 6

The reaction was carried out as in example 9A except 0.46 g of the Rh catalyst from above was used. Propylene/CO/H$_2$=4/4/4 cc/min. for 70 hr, 40 min. Propylene/CO/H2=2/2/2 cc/min. for additional 23 hr. The average linear/branch ratio (n-butyraldehyde/isobutyraldehyde) was about 1.6.

Example 11B

Hydroformylation of 3-Pentenenitrile Using Branched Polymer6

Reaction was run as in example 5A but with 1.5 equivalent of bidentate phosphite and Rh with branched polymer6. GC analysis: 60% conversion of 3-pentenenitrile; linearity of aldehydes produced: 40%; selectivity to 5-formylvaleronitrile: 31%.

Examples 12–18

Branched Polymers

Additional examples are described in the table. The branched polymers were prepared as described in example 5 or 6. The first diol is used to prepare the phosphochloridite and the second diol is used for further reaction. The diols used in these examples are listed below.

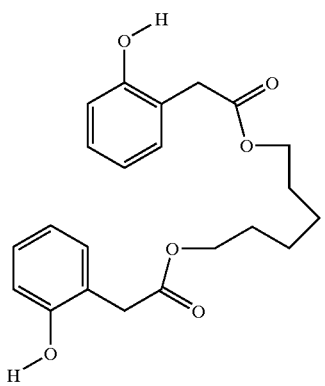

diol 1 diol 2
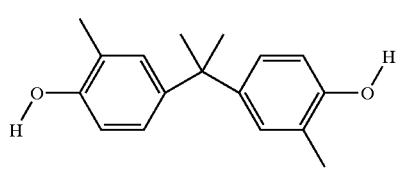

diol 3
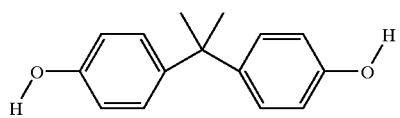

diol 4
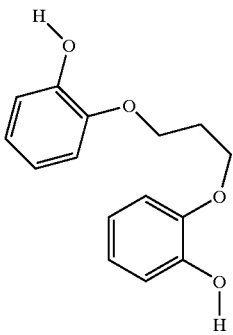

diol 5
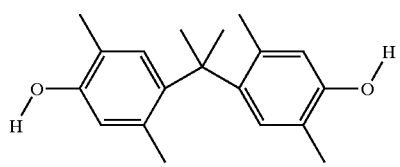

diol 6
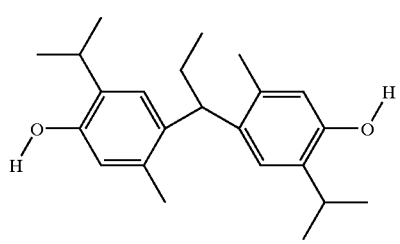

diol 7
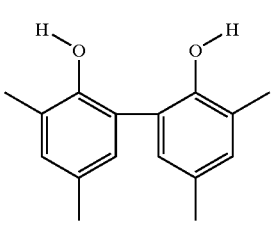

diol 8
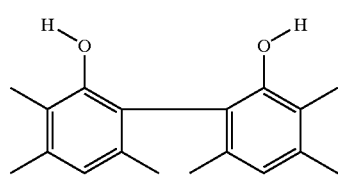

diol 9
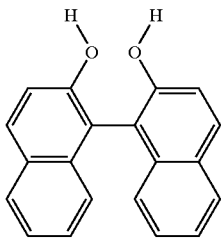

diol 10
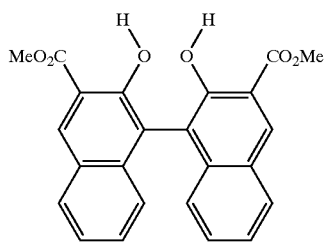

diol 11
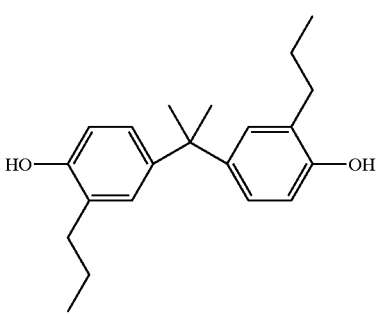

The hydroformylation of 3-pentenenitrile reactions were run as in example 5A except that the amounts of the specific polymer ligands shown in the Table 1 below. In the table, L/M denotes moles of ligand/moles of Rh; Conv. denotes conversion; Sel. refers to selectivity to; and Lin. is

TABLE 1

Hydroformylation of 3-Pentenenitrile

| Example | base | first diol | second diol | L/M | Conv. | Sel. | Lin. |
| --- | --- | --- | --- | --- | --- | --- | --- |
| 12 | NEt₃ | diol 1 | diol 7 | 3 | 95% | 70% | 81% |
| 13 | NEt₃ | diol 2 | diol 8 | 1.5 | 96% | 37% | 43% |
| 14 | NEt₃ | diol 4 | diol7 | 1.5 | 99% | 54% | 65% |
| 15 | N(Bu)₃ | diol 5 | diol7 | 3 | 89% | 46% | 55% |
| 16 | NEt₃ | diol 3 | diol10 | 1.5 | 97% | 42% | 47% |
| 17 | NEt₃ | diol 6 | diol9 | 1.5 | 98% | 39% | 47% |

The hydroformylation of methyl 3-pentenoate reactions were run as in example 4B with the exception that the amounts of the specific polymer ligands shown in Table 2.

TABLE 2

Hydroformylation of Methyl 3-Pentenoate

| Example | base | first diol | second diol | L/M | Conv. | Sel. | Lin. |
| --- | --- | --- | --- | --- | --- | --- | --- |
| 18 | NEt₃ | diol 2 | diol 10 | 4 | 95% | 73% | 81% |
| 19 | NEt₃ | diol 1 | diol 7 | 3 | 45% | 58% | 92% |
| 20 | N(Bu)₃ | diol 6 | diol 7 | 3 | 49% | 66% | 81% |
| 21 | N(Bu)₃ | diol 5 | diol 7 | 4 | 61% | 68% | 82% |

TABLE 2-continued

Hydroformylation of Methyl 3-Pentenoate

| Example | base | first diol | second diol | L/M | Conv. | Sel. | Lin. |
|---------|------|------------|-------------|-----|-------|------|------|
| 22 | N(Bu)$_3$ | diol 5 | diol 8 | 4 | 81% | 65% | 82% |
| 23 | N(Bu)$_3$ | diol 11 | diol 7 | 4 | 74% | 72% | 86% |
| 24 | N(Bu)$_3$ | diol 11 | diol 8 | 4 | 77% | 64% | 79% |

That which is claimed is:

1. A process comprising contacting an unsaturated organic compound, in the presence of a catalyst composition, with a fluid comprising carbon monoxide and hydrogen wherein said catalyst composition comprises a Group VIII metal and a polymeric phosphite composition, wherein said polymeric phosphite composition is selected from the group consisting of polymer A, polymer B, and combinations thereof;

said polymer A comprises repeat units derived from (1) a carbonyl compound, (2) a monomer, and (3) phosphochloridite;

said polymer B comprises repeat units derived from (1) phosphorus trichloride, (2) a polyhydric alcohol, and (3) an aromatic diol;

said carbonyl compound is selected from the group consisting of $(R^1O_2C)_m(OH)$—$Ar^1$—$(OH)(CO_2R^1)_m$, $(R^1O_2C)_m(OH)$—$Ar^2$—$A^2$—$Ar^2$—$(OH)(CO_2R^1)_m$, $(R^1O_2C)_m(OH)$—$Ar^2$—$Ar^2$—$(OH)(CO_2R^1)_m$, and combinations of two or more thereof;

said monomer is selected from the group consisting of polyhydric alcohol, amine, and combinations thereof;

said phosphochloridite has the formula $ClP(O$—$Ar^2$—$R^2)_2$ in which the $Ar^2$ groups are unlinked to each other, directly linked to each other, or linked to each other through group $A^2$;

each $Ar^1$ is selected from the group consisting of phenylene group, biphenylene group, naphthylene group, binaphthylene group, and combinations of two or more thereof;

each $Ar^2$ is independently selected from the group consisting of phenylene group, naphthylene group, and combinations thereof;

each $A^2$ is independently selected from the group consisting of —$C(R^1)(R^1)$—, —O—, —$N(R^1)$—, —S—, —$S(O)_2$—, —$S(O)$—, and combinations of two or more thereof;

each $R^1$ is independently selected from the group consisting of hydrogen, $C_1$ to $C_{12}$ alkyl or cycloalkyl group, $C_6$ to $C_{20}$ aryl group, and combinations of two or more thereof;

each $R^2$ is independently selected from the group consisting of hydrogen, $C_1$ to $C_{12}$ alkyl or cycloalkyl group, acetal, ketal, —$OR^3$, —$CO_2R^3$, $C_6$ to $C_{20}$ aryl group, F, Cl, —$NO_2$, —$SO_3R^3$, —CN, perhaloalkyl, —$S(O)R^3$, —$S(O)_2R^3$, —CHO, —$C(O)R^3$, cyclic ether, —$A^1Z$, and combinations of two or more thereof;

Z is selected from the group consisting of —$CO_2R^3$, —CHO, —$C(O)R^3$, —$C(O)SR^3$, —SR—$C(O)N(R^1)R^1$, —$OC(O)R^3$, —$OC(O)OR^3$, —N=$C(R^1)R^1$, —$C(R^1)$=$NR^1$, —$C(R^1)$=N—O—$R^1$, —$P(O)(OR^3)(OR^3)$, —$S(O)_2R^3$, —$S(O)R^3$, —$C(O)OC(O)R^3$, —$NR^3CO_2R^3$, —$NR^3C(O)N(R^1)R^1$, F, Cl, —$NO_2$, —$SO_3R^3$, perhaloalkyl, —CN, and combinations of two or more thereof;

$A^1$ is a $C_1$ to $C_{12}$ aklylene group;

each $R^3$ is independently selected from the group consisting of $C_1$ to $C_{12}$ alkyl or cycloalkyl group, $C_6$ to $C_{20}$ aryl group, and combinations thereof; and each m is independently a number in the range of from 1 to 2.

2. A process according to claim 1 wherein said unsaturated organic compound is selected from the group consisting of methyl 3-pentenoate, methyl 4-pentenoate, 3-pentenoic acid, 3-pentenenitrile, 4-pentenenitrile, 3-pentenal, allyl alcohol, and combinations of two or more thereof.

3. A process according to claim 1 wherein said unsaturated organic compound is methyl-3-pentenoate.

4. A process according to claim 1 wherein said unsaturated organic compound is selected from the group consisting of 3-pentenenitrile, 4-pentenenitrile, and combinations thereof.

5. A process according to claim 1 wherein, in the catalyst composition, said polymer is polymer A; and the $R^2$ group in $ClP(O$—$Ar^2$—$R^2)_2$ is ortho to the oxygen.

6. A process according to claim 1 wherein, in the catalyst composition, said monomer is a polyhydric alcohol having a formula selected from the group consisting of $(HO)_m$—$A^1$—$(OH)_m$, $(HO)_m$—$Ar^2$—$A^1$—$Ar^2$—$(OH)_m$, $(HO)_m$—$Ar^2$—$(O)$—$A^1$—$(O)$—$Ar^2$—$(OH)_m$, $(HO)_m$—$(A^1$—$O)_p$—$A^1$—$(OH)_m$, $(HO$—$A^1)_m(OH)$—$Ar^1$—$(OH)(A^1$—$OH)_m$, $(HO$—$A^1)_m(OH)$—$Ar^2$—$A^2$—$Ar^2$—$(OH)(A^1$—$OH)_m$, $(HO$—$A^1)_m(OH)$—$Ar^2$—$Ar^2$—$(OH)(A^1$—$OH)_m$, $(HO)_m$—$Ar^2$—$(O$—$A^1)_p$—$O$—$Ar^2$—$(OH)_m$, $(OH)_m$—$Ar^2$—$Ar^2$—$(OH)_m$, $(OH)_m$—$Ar^2$—$A^2$—$Ar^2$—$(OH)_m$, $(HO)_m$—$Ar^2$—$A^1$—$C(O)$—$O$—$A^1$—$O$—$C(O)$—$A^1$—$Ar^2$—$(OH)_m$, $(OH)$—$Ar^1$—$(OH)$, and combinations of two or more—thereof;

$A^2$, $Ar^1$, $Ar^2$, and m are the same as recited in claim 1;

each $A^1$ is independently a $C_1$ to $C_{12}$ alkylene group; and each p is independently a number in the range of from 1 to 10.

7. A process according to claim 6 wherein, in the catalyst composition, said polyhydric alcohol is selected from the group consisting of 1,3-propananediol, tetra(ethylene glycol), 1,6-hexanediol, 1,4-cyclohexanediol, 2,6-dihydroxynaphthalene, hexa(ethylene glycol), and combinations of two or more thereof.

8. A process according to claim 1 wherein, in the catalyst composition, said monomer is an amine selected from the group consisting of diamines, triamines, tetraamines, and combinations of two or more thereof.

9. A process according to claim 8 wherein, in the catalyst composition, said amine is selected from the group consisting of 1,6-hexadiamine, N,N'-dimetehylhexanediamine, 1,4-butanediamine, and combinations of two or more thereof.

10. A process according to claim 1 wherein, in the catalyst composition, said carbonyl compound is selected from the group consisting of

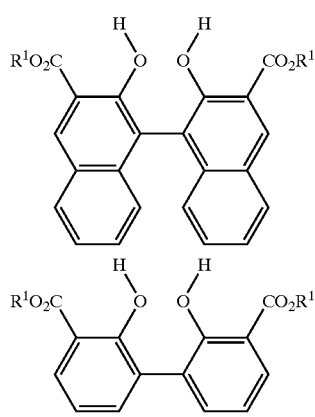

and combinations thereof; and $R^1$ is the same as recited in claim 1.

11. A process according to claim 10 wherein, in the catalyst composition, said carbonyl compound is selected from the group consisting of dialkyl 2,2'-dihydroxyl-1,1'-binaphthalene-3,3'-dicarboxylate, dialkyl 2,2'-dihydroxyl-1,1'-biphenyl-3,3'-dicarboxylate, 2,2'-dihydroxy-biphenyl-3,3'-dicarboxylic acid, 2,2'-dihydroxy-1,1'-binaphthyl-3,3'-dicarboxylic acid, terephthalic acid, isophthalic acid, phthalic acid, dimethyl isophthalate, dimethyl phthalate, dimethyl terephthalate, 1,3,5-benzenetricarboxylic acid, and combinations of two or more thereof.

12. A process according to claim 1 wherein, in the catalyst composition, said polymer is polymer B.

13. A process according to claim 1 wherein, in the catalyst composition, said aromatic diol has the formula selected from the group consisting of

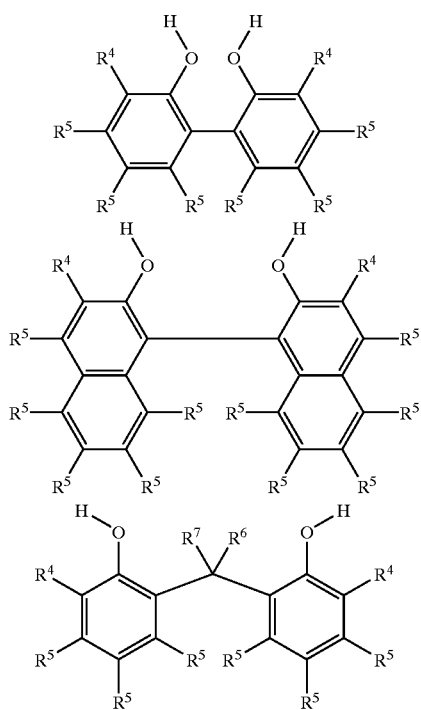

wherein
each $R^4$ is independently selected from the group consisting of hydrogen, $C_1$ to $C_{12}$ alkyl or cycloalkyl group, acetal, ketal, —$OR^3$, —$CO_2R^3$, $C_6$ to $C_{20}$ aryl group, —$SiR^3$, —$NO_2$, —$SO_3R^3$, —$S(O)R^3$, —$S(O)_2R^3$, —CHO, —$C(O)R^3$, —F, —Cl, —CN, perhaloalkyl, —$C(O)N(R^3)(R^3)$, —$A^1Z$, and combinations of two or more thereof;

Z is independently selected from the group consisting of —$CO_2R^3$, —CHO, —$C(O)R^3$, —$C(O)SR^3$, —$SR^3$, —$C(O)N(R^1)R^1$, —$OC(O)R^3$, —$OC(O)OR^3$, —N=C$(R^1)R^1$, —$C(R^1)$=$NR^1$, —$C(R^1)$=N—O—$R^1$, —$P(O)(OR^3)(OR^3)$, —$S(O)_2R^3$, —$S(O)R^3$, —$C(O)OC(O)R^3$, —$NR^3CO_2R^3$, —$NR^3C(O)N(R^1)R^1$, F, Cl, —$NO_2$, —$SO_3R^3$, —CN, and combinations of two or more thereof;

$A^1$ and $R^3$ are the same as recited in claim 1;

each $R^5$ independently is H, F, Cl, $C_1$ to $C_{12}$ alkyl or cycloalkyl group, $C_6$ to $C_{20}$ aryl group, —$OR^3$, —$CO_2R^3$, —$C(O)R^3$, —CHO, —CN, —$CF_3$, and combinations of two or more thereof;

each $R^6$ independently is selected from the group consisting of H, $C_1$ to $C_{12}$ alkyl or cycloalkyl, $C_6$ to $C_{20}$ aryl, and combinations of two or more thereof; and each $R^7$ independently is selected from the group consisting of H, $C_1$ to $C_{12}$ alkyl or cycloalkyl, $C_6$ to $C_{20}$ aryl, and combinations of two or more thereof.

14. A process according to claim herein, in the catalyst composition, said polyhydric alcohol (a) is selected from the group consisting of $(R^4)(HO)_m$—$Ar^2$—$A^1$—$Ar^2$—$(OH)_m$$(R^4)$, $(R^4)(HO)_m$—$Ar^2$—$(O$—$A^1)_p$—$O$—$Ar^2$—$(OH)_m(R^4)$, $(R^4)(OH)_m$—$Ar^2$—$Ar^2$—$(OH)_m(R^4)$, $(R^4)(OH)_m$—$Ar^2$—$A^2$—$Ar^2$—$(OH)_m(R^4)$, $(R^4)(HO)_m$—$Ar^2$—$A^1$—$C(O)$—$O$—$A^1$—$O$—$C(O)$—$A^1$—$Ar^2$—$(OH)_m(R^4)$, $(R^4)(OH)_m$—$Ar^1$—$(OH)_m(R^4)$, and combinations of two or more thereof;

$A^2$, $Ar^1$, $Ar^2$, and m are the same as recited in claim 1;

each $A^1$ is independently a $C_1$ to $C_{12}$ aklylene groups;

each $R^4$ is the same as recited in claim 13; and p is a number of 1 to 10; or (b) is selected from the group consisting of $(OH)_mAr^1$—$R^4$—$R^4$—$Ar^1(OH)_m$ and $(OH)_mAr^1$—$R^4$—$A^1$—$R^4$—$Ar^1(OH)_m$;

$Ar^1$ and $A^1$ are the same as recited in claim 1; and each $R^4$ is independently selected from the group consisting of $C_1$ to $C_{12}$ alkyl or cycloalkyl group, acetal, ketal, —$OR^3$, $CO_2R^3$, $C_6$ to $C_{20}$ aryl group, —$SiR^3$, —$SO_3R^3$, —$S(O)R^3$, —$S(O)_2R^3$, perhaloalkyl, —$C(O)N(R^3)(R^3)$, —$A^1CO_2R^3$, —$A^1OR^3$ and combinations of two or more thereof.

15. A process according to claim 14 wherein, in the catalyst composition, the location of the OH groups of said polyhydric alcohol are placed such that, when said polyhydric alcohol is contacted with $PCl_3$, monodentate phosphites are not predominantly produced.

16. A process according to claim 14 wherein, in the catalyst composition, said polyhydric alcohol is selected from the group consisting of
6,6'-dihydroxy-4,4,4',7,7,7'-hexamethyl bis-2,2'-spirochroman,
2,2'-diallylbisphenolA, bisphenol A,
4,4'-(1-methylethylidene)bis(2-(1-methylpropyl)phenol),
4,4'-thiophenol, 4,4'-dihydroxydiphenylsulfone,
4,4'-sulfonylbis(2-methylphenol),
bis(4-hydroxy-3-methylphenyl) sulfide,
2'-dis(4-hydroxy-3-methylphenyl)propane,
4,4'-ethylidenebis(2,5-dimethylphenol), 4,4'-propylidenebis(2,5-dimethylphenol),
4,4'-benzylidenebis(2,5-dimethylphenol),
4,4'-ethylidenebis(2-isopropyl-5-methylphenol),

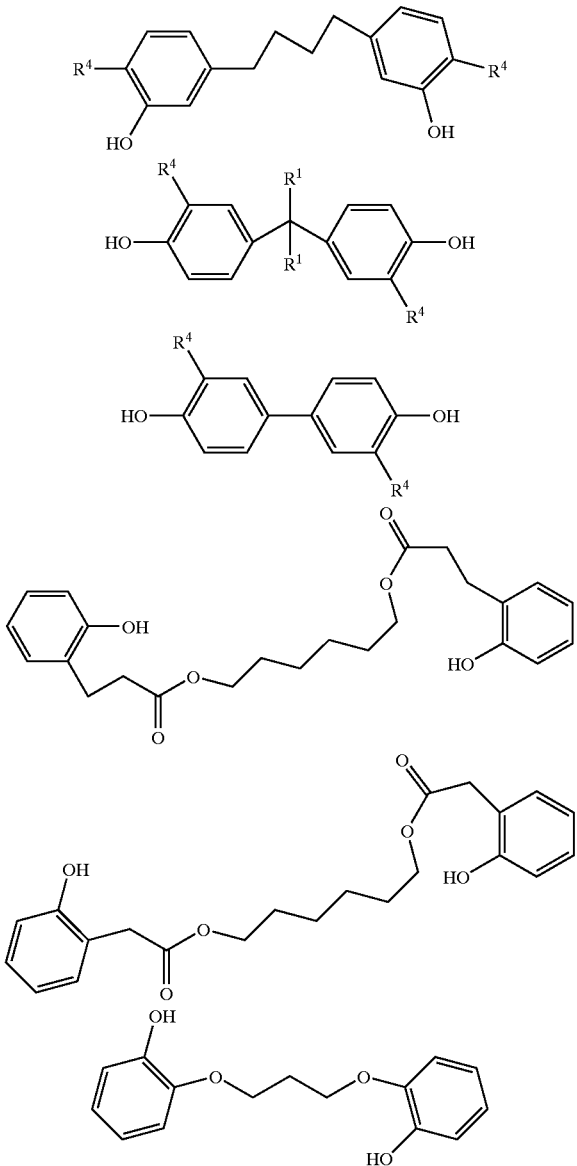

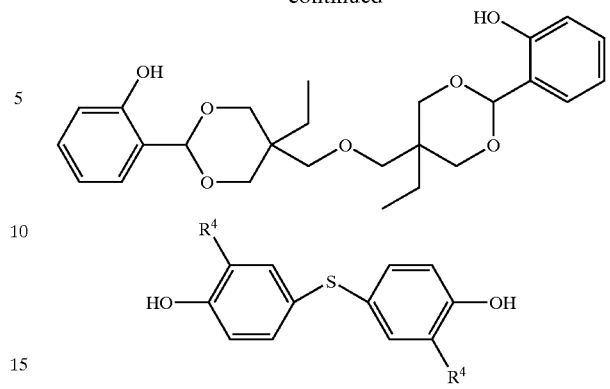

and combinations of two or more thereof.

17. A process according to claim 1 wherein, in the catalyst composition, said Group VIII metal is selected from the group consisting of Rh, Ir, Ru, Pt, and combinations of two or more thereof.

18. A process according to claim 1 wherein, in the catalyst composition, said Group VIII metal is Rh.

19. A process according to claim 1 wherein, in the catalyst composition, said Group VIII metal is selected from the group consisting of rhodium hydride, rhodium halide, rhodium organic acid salt, rhodium ketonate, rhodium inorganic acid salt, rhodium oxide, rhodium carbonyl compound, rhodium amine compound, and combinations of two or more thereof.

20. A process according to claim 1 wherein, in the catalyst composition, said Group VIII metal is selected from the group consisting of $Ir_4(CO)_{12}$, $IrSO_4$, $RhCl_3$, $Rh(NO_3)_3$, $Rh(acetate)_3$, $Rh_2O_3$, rhodium bis(carbonyl)acetylacetonate, $(Rh(acetate)(1,5\text{-cyclooctadiene})]_2$, $Rh_4(CO)12$, $Rh_6(CO)_{16}$, $RhH(CO)(Ph_3P)_3$, $[Rh(acetate)(CO)_2]_2$, $[RhCl(1,5\text{-cyclooctadiene})]2$, and combinations of two or more thereof.

21. A process according to claim 1 wherein, in the catalyst composition, said Group VIII metal is rhodium bis(carbonyl)acetylacetonate.

* * * * *